(12) United States Patent
Eckhardt et al.

(10) Patent No.: US 7,393,836 B2
(45) Date of Patent: Jul. 1, 2008

(54) D-XYLOPYRANOSYL-SUBSTITUTED PHENYL DERIVATIVES, MEDICAMENTS CONTAINING SUCH COMPOUNDS, THEIR USE AND PROCESS FOR THEIR MANUFACTURE

(75) Inventors: Matthias Eckhardt, Biberach (DE); Frank Himmelsbach, Mittelbiberach (DE); Peter Eickelmann, Mittelbiberach (DE); Leo Thomas, Biberach (DE); Edward Leon Barsoumian, Toyonaka (JP)

(73) Assignee: Boehringer Ingelheim International GmbH, Ingelheim (DE)

( * ) Notice: Subject to any disclaimer, the term of this patent is extended or adjusted under 35 U.S.C. 154(b) by 204 days.

(21) Appl. No.: 11/168,905

(22) Filed: Jun. 28, 2005

(65) Prior Publication Data

US 2006/0009400 A1    Jan. 12, 2006

(30) Foreign Application Priority Data

Jul. 6, 2004   (DE) ................. 10 2004 032 823
Nov. 11, 2004  (DE) ................. 10 2004 054 603

(51) Int. Cl.
*A01N 43/04*  (2006.01)
*A61K 31/70*  (2006.01)
*C07H 1/00*   (2006.01)

(52) U.S. Cl. ........................ 514/23; 536/1.11
(58) Field of Classification Search ........ None
See application file for complete search history.

(56) References Cited

U.S. PATENT DOCUMENTS 6,414,126 B1 * 7/2002 Ellsworth et al. ........ 536/17.2

2006/0019948 A1   1/2006  Eckhardt et al.

FOREIGN PATENT DOCUMENTS

| WO | WO 98/31697      | 7/1998  |
| WO | WO 01/27128 A1   | 4/2001  |
| WO | WO 02/083066 A   | 10/2002 |
| WO | WO 03/099836 A   | 12/2003 |
| WO | WO 2004/013118 A1| 2/2004  |
| WO | WO 2004/052902 A1| 6/2004  |
| WO | WO 2004/052903 A1| 6/2004  |
| WO | WO 2004/080990 A1| 9/2004  |
| WO | WO 2005/012326 A1| 2/2005  |

OTHER PUBLICATIONS

Adachi et al., "T-1095, a Renal Na+-Glucose Transport Inhibitor", Metabolism, vol. 49 (8), 2000, 990-995.*

* cited by examiner

*Primary Examiner*—Shaojia Anna Jiang
*Assistant Examiner*—Traviss C. McIntosh, III
(74) *Attorney, Agent, or Firm*—David A. Dow; Michael P. Morris; Mary-Ellen M. Devlin

(57) ABSTRACT

A D-Xylopyranosyl-substituted phenyl compound of general formula I

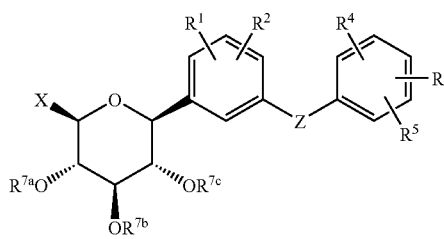

wherein the groups $R^1$ to $R^5$, X, Z and $R^{7a}$, $R^{7b}$, $R^{7c}$ are defined as in claim 1, have an inhibiting effect on the sodium-dependent glucose cotransporter SGLT. The present invention also relates to pharmaceutical compositions for the treatment of metabolic disorders.

24 Claims, No Drawings

D-XYLOPYRANOSYL-SUBSTITUTED PHENYL DERIVATIVES, MEDICAMENTS CONTAINING SUCH COMPOUNDS, THEIR USE AND PROCESS FOR THEIR MANUFACTURE

RELATED APPLICATIONS

This application claims benefit of German Patent Application DE 10 2004 032 823.4, filed Jul. 6, 2004, and German Patent Application DE 10 2004 054 603.7, filed Nov. 11, 2004.

FIELD OF THE INVENTION

The present invention relates to D-xylopyranosyl-substituted phenyls of general formula I

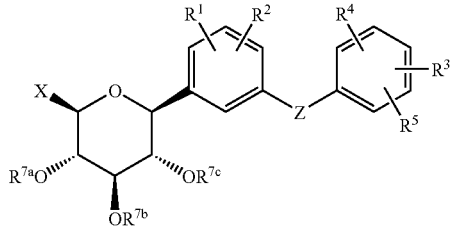

wherein the groups $R^1$ to $R^5$, X, Z and $R^{7a}$, $R^{7b}$, $R^{7c}$ are as hereinbefore defined, including the tautomers, the stereoisomers, the mixtures thereof and the salts thereof. The invention further relates to pharmaceutical compositions containing a compound of formula I as well as the use of a compound according to the invention for preparing a pharmaceutical composition for the treatment of metabolic disorders. The invention also relates to processes for preparing a pharmaceutical composition and a compound according to the invention.

Compounds which have an inhibitory effect on sodium-dependent glucose cotransporter SGLT are proposed in the literature for the treatment of diseases, particularly diabetes.

Glucopyranosyl-substituted aromatic groups and the preparation thereof and their possible activity as SGLT2 inhibitors are known from published International Patent Applications WO 98/31697, WO 01/27128, WO 02/083066, WO 03/099836, WO 04/13118, WO 04/80990, WO 04/52902, WO 04/52903 and WO 05/12326.

PROBLEM OF THE INVENTION

The aim of the present invention is to indicate new pyranosyl-substituted phenyls, particularly those which have an effect on sodium-dependent glucose cotransporter SGLT, particularly SGLT2. A further aim of the present invention is to indicate pyranosyl-substituted phenyls which, by comparison with known structurally similar compounds, have a greater inhibitory effect on the sodium-dependent glucose cotransporter SGLT2 in vitro and/or in vivo and/or have improved pharmacological or pharmacokinetic properties.

Moreover the present invention also sets out to prepare new pharmaceutical compositions which are suitable for the prevention and/or treatment of metabolic disorders, particularly diabetes.

The invention also relates to a process for preparing the compounds according to the invention.

Further aims of the present invention will immediately become apparent to the skilled man from the remarks above and hereinafter.

OBJECT OF THE INVENTION

In a first aspect the invention relates to D-xylopyranosyl-substituted phenyls of general formula I

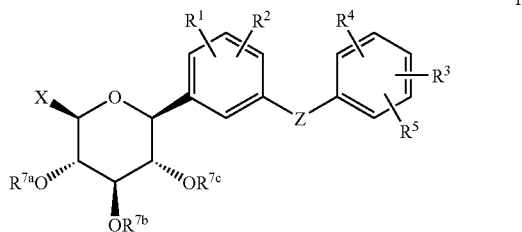

wherein $R^1$ denotes hydrogen, fluorine, chlorine, bromine, $C_{1-6}$-alkyl, $C_{2-6}$-alkynyl, $C_{2-6}$-alkenyl, $C_{3-7}$-cycloalkyl, $C_{3-7}$-cycloalkyl-$C_{1-3}$-alkyl, $C_{5-7}$-cycloalkenyl, $C_{5-7}$-cycloalkenyl-$C_{1-3}$-alkyl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, $C_{1-4}$-alkoxycarbonyl, amino, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, $C_{1-6}$alkyloxy, $C_{3-7}$-cycloalkyloxy, $C_{5-7}$-cycloalkenyloxy, aryloxy, $C_{1-4}$-alkylsulphanyl, $C_{1-4}$-alkylsulphinyl, $C_{1-4}$-alkylsulphonyl, $C_{3-7}$-cycloalkylsulphanyl, $C_{3-7}$-cycloalkylsulphinyl, $C_{3-7}$-cycloalkylsulphonyl, $C_{5-7}$-cycloalkenylsulphanyl, $C_{5-7}$-cycloalkenylsulphinyl, $C_{5-7}$-cycloalkenylsulphonyl, arylsulphanyl, arylsulphinyl, arylsulphonyl, hydroxy, cyano or nitro, while alkyl, alkenyl, alkynyl, cycloalkyl and cycloalkenyl groups may be partly or completely fluorinated or may be mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, and $R^2$ denotes hydrogen, fluorine, chlorine, bromine, hydroxy, $C_{1-4}$-alkyl, $C_{1-4}$-alkoxy, cyano or nitro, while alkyl groups may be mono- or polysubstituted by fluorine, or in the event that $R^1$ and $R^2$ are bound to two C atoms of the phenyl ring which are adjacent to one another, $R^1$ and $R^2$ may be joined together in such a way that $R^1$ and $R^2$ together form a $C_{3-5}$-alkylene or $C_{3-5}$-alkenylene bridge which may be partly or totally fluorinated or mono- or disubstituted by identical or different substituents selected from chlorine, hydroxy, $C_{1-3}$-alkoxy and $C_{1-3}$-alkyl and wherein one or two methylene groups may be replaced independently of one another by O, S, CO, SO, $SO_2$ or $NR^N$, $R^3$ denotes hydrogen, fluorine, chlorine, bromine, $C_{1-6}$-alkyl, $C_{2-6}$-alkynyl, $C_{2-6}$-alkenyl, $C_{3-7}$-cycloalkyl, $C_{3-7}$-cycloalkyl-$C_{1-3}$-alkyl, $C_{5-7}$-cycloalkenyl, $C_{5-7}$-cycloalkenyl-$C_{1-3}$-alkyl, aryl, heteroaryl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperid in-1-ylcarbonyl, morpholin-4-ylcarbonyl, piperazin-1-ylcarbonyl, 4-($C_{1-4}$-alkyl)piperazin-1-ylcarbonyl, hydroxycarbonyl, $C_{1-4}$-alkoxycarbonyl, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, arylcarbonylamino, heteroarylcarbonylamino, $C_{1-4}$-alkylsulphonylamino, arylsulphonylamino, $C_{1-6}$-alkoxy, $C_{3-7}$-cycloalkyloxy, $C_{5-7}$-cycloalkenyloxy, aryloxy, heteroaryloxy, $C_{1-4}$-alkylsulphanyl, $C_{1-4}$-alkylsulphinyl, $C_{1-4}$-alkylsulphonyl, $C_{3-7}$-cycloalkylsulphanyl, $C_{3-7}$-cycloalkylsulphinyl, $C_{3-7}$-cycloalkylsulphonyl, $C_{5-7}$-cycloalkenylsulphanyl, $C_{5-7}$-cycloalkenylsulphinyl, $C_{5-7}$-cycloalkenylsulphonyl, arylsulphanyl, arylsulphinyl, arylsulphonyl, amino, hydroxy, cyano or nitro, while alkyl, alkenyl, alkynyl, cycloalkyl and cycloalkenyl groups may be partly or totally fluorinated or mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, and $R^4$ denotes hydrogen, fluorine, chlorine, bromine, iodine, cyano, nitro, $C_{1-3}$-alkyl, $C_{1-3}$-alkoxy or methyl or methoxy substituted by 1 to 3 fluorine atoms, or in the event that $R^3$ and $R^4$ are bound to two C atoms of the phenyl ring which are adjacent to one another, $R^3$ and $R^4$ may be joined together in such a way that $R^3$ and $R^4$ together form a $C_{3-5}$-alkylene or $C_{3-5}$-alkenylene bridge, which may be partly or totally fluorinated or mono- or disubstituted by identical or different substituents selected from chlorine, hydroxy, $C_{1-3}$-alkoxy and $C_{1-3}$-alkyl and wherein one or two methylene groups may be replaced independently of one another by O, S, CO, SO, $SO_2$ or $NR^N$, $R^5$ denotes hydrogen, fluorine, chlorine, bromine, iodine, cyano, nitro, $C_{1-3}$-alkyl, $C_{1-3}$-alkoxy or methyl or methoxy substituted by 1 to 3 fluorine atoms, and $R^N$ independently of one another denote H or $C_{1-4}$-alkyl, L are selected independently of one another from among fluorine, chlorine, bromine, iodine, $C_{1-3}$-alkyl, difluoromethyl, trifluoromethyl, $C_{1-3}$-alkoxy, difluoromethoxy, trifluoromethoxy and cyano, $R^{7a}$, $R^{7b}$, $R^{7c}$ independently of one another have a meaning selected from among hydrogen, ($C_{1-18}$-alkyl)carbonyl, ($C_{1-18}$-alkyl)oxycarbonyl, arylcarbonyl and aryl-($C_{1-3}$-alkyl)-carbonyl, X denotes hydrogen, $C_{1-6}$-alkyl, $C_{2-6}$-alkynyl, $C_{2-6}$-alkenyl, $C_{3-7}$-cycloalkyl, $C_{3-7}$-cycloalkyl-$C_{1-3}$-alkyl, $C_{5-7}$-cycloalkenyl, $C_{5-7}$-cycloalkenyl-$C_{1-3}$-alkyl, aryl, aryl-$C_{1-3}$-alkyl, heteroaryl, heteroaryl-$C_{1-3}$-alkyl, $C_{1-4}$-alkylcarbonyl, arylcarbonyl, aminocarbonyl, $C_{1-4}$-alkylaminocarbonyl, di-($C_{1-3}$-alkyl)aminocarbonyl, (aryl-$C_{1-3}$-alkyl)aminocarbonyl, pyrrolidin-1-ylcarbonyl, piperidin-1-ylcarbonyl, morpholin-4-ylcarbonyl, hydroxycarbonyl, $C_{1-4}$-alkoxycarbonyl, $C_{1-4}$-alkylcarbonylamino-$C_{1-3}$-alkyl, N-($C_{1-4}$-alkylcarbonyl)-N-($C_{1-3}$-alkyl)-amino-$C_{1-3}$-alkyl, arylcarbonylamino-$C_{1-3}$-alkyl, $C_{1-4}$-alkylsulphonylamino-$C_{1-3}$-alkyl, arylsulphonylamino-$C_{1-3}$-alkyl, $C_{1-6}$-alkoxy-$C_{1-3}$-alkyl, $C_{3-7}$-cycloalkyloxy-$C_{1-3}$-alkyl, $C_{5-7}$-cycloalkenyloxy-$C_{1-3}$-alkyl, aryloxy-$C_{1-3}$-alkyl, heteroaryloxy-$C_{1-3}$-alkyl, $C_{1-4}$-alkylsulphanyl-$C_{1-3}$-alkyl, $C_{1-4}$-alkylsulphinyl-$C_{1-3}$-alkyl, $C_{1-4}$-alkylsulphonyl, $C_{1-4}$-alkylsulphonyl, $C_{1-4}$-alkylsulphonyl-$C_{1-3}$-alkyl, $C_{1-4}$-arylsulphanyl-$C_{1-3}$-alkyl, arylsulphonyl-$C_{1-3}$-alkyl, aryl-$C_{1-3}$-alkyl-sulphonyl-$C_{1-3}$-alkyl, $C_{1-4}$-alkylsulphonyloxy-$C_{1-3}$-alkyl, arylsulphonyloxy-$C_{1-3}$-alkyl, aryl-$C_{1-3}$-alkyl-sulphonyloxy-$C_{1-3}$-alkyl, $C_{3-7}$-cycloalkylsulphanyl-$C_{1-3}$-alkyl, $C_{3-7}$-cycloalkylsulphinyl, $C_{3-7}$-cycloalkylsulphonyl, $C_{5-7}$-cycloalkenylsulphanyl-$C_{1-3}$-alkyl, $C_{5-7}$-cycloalkenylsulphinyl, $C_{5-7}$-cycloalkenylsulphonyl, $C_{1-4}$-alkylcarbonylsulphanyl-$C_{1-3}$-alkyl or cyano, while alkyl, alkenyl, alkynyl, cycloalkyl and cycloalkenyl groups may be partly or totally fluorinated or mono- or disubstituted by identical or different substituents selected from chlorine, cyano, hydroxy, mercapto, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, and X representing hydroxymethyl is excluded, Z denotes oxygen, methylene, dimethylmethylene, difluoromethylene or carbonyl;

while the term aryl groups used in the definition of the above groups denotes phenyl or naphthyl groups, which may be mono- or disubstituted independently of one another by identical or different groups L; and the term heteroaryl groups used in the definition of the above-mentioned groups denotes a pyrrolyl, furanyl, thienyl, pyridyl, indolyl, benzofuranyl, benzothiophenyl, quinolinyl or isoquinolinyl group, or a pyrrolyl, furanyl, thienyl, pyridyl or imidazolyl group, wherein one or two methyne groups are replaced by nitrogen atoms, or an indolyl, benzofuranyl, benzothiophenyl, quinolinyl or isoquinolinyl group, wherein one to three methyne groups are replaced by nitrogen atoms, while the above-mentioned heteroaryl groups may be mono- or disubstituted independently of one another by identical or different groups L;

while by the N-heterocycloalkyl group mentioned in the definition of the above-mentioned groups is meant a saturated carbocyclic ring which comprises an imino group in the ring, which may comprise another optionally substituted imino group or an O or S atom in the ring, and unless otherwise stated the above-mentioned alkyl groups may be straight-chain or branched, the tautomers, the stereoisomers, the mixtures thereof and the salts thereof, particularly the physiologically acceptable salts thereof.

The compounds according to the invention of general formula I and the physiologically acceptable salts thereof have valuable pharmacological properties, particularly an inhibitory effect on the sodium-dependent glucose cotransporter SGLT, particularly SGLT2. Moreover compounds according to the invention may have an inhibitory effect on the sodium-dependent glucose cotransporter SGLT1. Compared with a possible inhibitory effect on SGLT1 the compounds according to the invention preferably inhibit SGLT2 selectively.

The present invention also relates to the physiologically acceptable salts of the compounds according to the invention with inorganic or organic acids.

Therefore, the invention also relates to the use of the compounds according to the invention, including the physiologically acceptable salts, as pharmaceutical compositions.

This invention also relates to pharmaceutical compositions, containing at least one compound according to the invention or a physiologically acceptable salt according to the invention, optionally together with one or more inert carriers and/or diluents.

A further subject of this invention is the use of at least one compound according to the invention or a physiologically or pharmaceutically acceptable salt of such a compound for preparing a pharmaceutical composition which is suitable for the treatment or prevention of diseases or conditions which can be influenced by inhibiting the sodium-dependent glucose cotransporter SGLT, particularly SGLT2.

This invention also relates to the use of at least one compound according to the invention for preparing a pharmaceutical composition which is suitable for the treatment of metabolic disorders.

This invention also relates to the use of at least one compound according to the invention for preparing a pharmaceutical composition for inhibiting the sodium-dependent glucose cotransporter SGLT, particularly SGLT2.

The invention further relates to a process for preparing a pharmaceutical composition according to the invention, characterised in that a compound according to the invention is incorporated in one or more inert carriers and/or diluents by a non-chemical method.

The present invention also relates to a process for preparing the compounds of general formula I according to the invention, characterised in that a) in order to prepare compounds of general formula I as defined hereinbefore and hereinafter,
a compound of general formula II wherein
R' denotes H, $C_{1-4}$-alkyl, $(C_{1-18}$-alkyl)carbonyl, $(C_{1-18}$-alkyl)oxycarbonyl, arylcarbonyl or aryl-$(C_{1-3}$-alkyl)-carbonyl, wherein the alkyl or aryl groups may be mono- or polysubstituted by halogen;

$R^{8a}$, $R^{8b}$, $R^{8c}$ independently of one another have one of the meanings given hereinbefore and hereinafter for the groups $R^{7a}$, $R^{7b}$, $R^{7c}$, denote a benzyl group or a $R^aR^bR^cSi$ group or a ketal or acetal group, particularly an alkylidene or arylalkylidene ketal or acetal group, while in each case two adjacent groups $R^{8a}$, $R^b$, $R^{8c}$, $R^{8d}$ may form a cyclic ketal or acetal group or a 1,2-di($C_{1-3}$-alkoxy)-1,2-di($C_{1-3}$-alkyl)-ethylene bridge, while the above-mentioned ethylene bridge together with two oxygen atoms and the associated two carbon atoms of the pyranose ring form a substituted dioxane ring, particularly a 2,3-dimethyl-2,3-di($C_{1-3}$-alkoxy)-1,4-dioxane ring, and while alkyl, aryl and/or benzyl groups may be mono- or polysubstituted by halogen or $C_{1-3}$-alkoxy and benzyl groups may also be substituted by a di-($C_{1-3}$-alkyl)amino group; and $R^a$, $R^b$, $R^c$ independently of one another represent $C_{1-4}$-alkyl, aryl or aryl-$C_{1-3}$-alkyl, wherein the aryl or alkyl groups may be mono- or polysubstituted by halogen;

while the term aryl groups used in the definition of the above groups denotes phenyl or naphthyl groups, preferably phenyl groups;

and wherein the groups X and $R^1$ to $R^5$ and the bridge Z are as defined above and hereinafter;

is reacted with a reducing agent in the presence of an acid, and any protective groups present are cleaved at the same time or subsequently; or b) in order to prepare compounds of general formula I wherein $R^{7a}$, $R^{7b}$ and $R^{7c}$ represent hydrogen,
in a compound of general formula III wherein X, Z, $R^{8a}$, $R^{8b}$, $R^{8c}$ and $R^1$ to $R^5$ are as defined above and hereinafter, and at least one of the groups $R^{8a}$, $R^{8b}$ and $R^{8c}$ does not denote hydrogen, the groups $R^{8a}$, $R^{8b}$ or $R^{8c}$ which do not represent hydrogen are removed, particularly hydrolysed; and if necessary any protective group used in the reactions described above according to method a) or b) is cleaved and/or if desired a compound of general formula I thus obtained is selectively derivatised at a hydroxy group or this group is substituted and/or if desired a compound of general formula I thus obtained is resolved into its stereoisomers and/or if desired a compound of general formula I thus obtained is converted into the salts thereof, particularly, for pharmaceutical use, into the physiologically acceptable salts thereof.

DETAILED DESCRIPTION OF THE INVENTION

Unless otherwise stated the groups, residues and substituents, particularly $R^1$ to $R^5$, X, Z, L, $R^N$, $R^{7a}$, $R^{7b}$, $R^{7c}$, are defined as above and hereinafter.

If residues, substituents or groups occur several times in a compound, they may have the same or different meanings.

The group $R^3$ is preferably in the meta or para position to the -Z- bridge, which means that compounds according to the following formulae I.1 and I.2, particularly

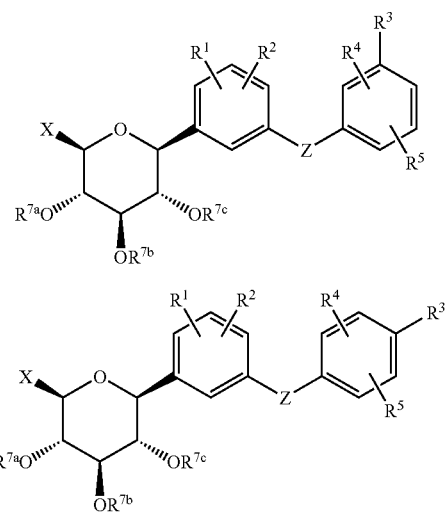

The term aryl used above and hereinafter, for example in the groups X, $R^1$ and $R^3$, preferably denotes phenyl. According to the general definition and unless otherwise stated, the aryl group, particularly the phenyl group, may be mono- or disubstituted by identical or different groups L.

The term heteroaryl used above and hereinafter, for example in the groups X, $R^1$ and $R^3$, preferably denotes pyridinyl, pyrimidinyl, pyridazinyl, pyrazinyl, triazinyl, imidazolyl, pyrazolyl, triazolyl, tetrazolyl, oxazolyl, oxadiazolyl, thiazolyl or thiadiazolyl. According to the general definition and unless otherwise stated, the heteroaryl group may be mono- or disubstitued by identical or different groups L.

Preferably $R^1$ denotes hydrogen, fluorine, chlorine, bromine, $C_{1-6}$-alkyl, $C_{2-6}$-alkynyl, $C_{2-6}$-alkenyl, $C_{3-7}$-cycloalkyl, $C_{5-7}$-cycloalkenyl, $C_{1-4}$-alkylcarbonyl, aminocarbonyl, $C_{1-4}$-alkylaminocarbonyl, di-($C_{1-3}$-alkyl)aminocarbonyl, $C_{1-4}$-alkoxycarbonyl, $C_{1-4}$-alkylamino, di-($C_{1-3}$-alkyl)amino, pyrrolidin-1-yl, piperidin-1-yl, morpholin-4-yl, $C_{1-4}$-alkylcarbonylamino, $C_{1-6}$-alkyloxy, $C_{3-7}$-cycloalkyloxy, $C_{5-7}$-cycloalkenyloxy, $C_{1-4}$-alkylsulphanyl, $C_{1-4}$-alkylsulphonyl, $C_{3-7}$-cycloalkylsulphanyl, $C_{3-7}$-cycloalkylsulphonyl, $C_{5-7}$-cycloalkenylsulphanyl, $C_{5-7}$-cycloalkenylsulphonyl, hydroxy and cyano, while alkyl, alkenyl, alkynyl, cycloalkyl and cycloalkenyl groups may be partly or totally fluorinated or mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$.

If the group $R^1$ denotes a cycloalkyl or cycloalkenyl group wherein one or two methylene groups are replaced independently of one another by O, S, CO, SO or $SO_2$, preferred meanings of the group $R^1$ are selected from among tetrahydrofuranyl, tetrahydrofuranonyl, tetrahydrothienyl, tetrahydropyranyl, tetrahydropyranonyl, dioxanyl and trioxanyl.

If the group $R^1$ denotes an N-heterocycloalkyl group wherein a methylene group is replaced by CO or $SO_2$, preferred meanings of the group $R^1$ are selected from among pyrrolidinone, piperidinone, piperazinone and morpholinone.

Particularly preferably $R^1$ denotes hydrogen, fluorine, chlorine, bromine, $C_{1-6}$-alkyl, $C_{2-6}$-alkynyl, $C_{2-6}$-alkenyl, $C_{3-7}$-cycloalkyl, $C_{5-7}$-cycloalkenyl, $C_{1-6}$-alkyloxy, $C_{3-7}$-cycloalkyloxy or cyano, while in cycloalkyl and cycloalkenyl groups one or two methylene units may be replaced independently of one another by O or CO and alkyl, alkenyl and alkynyl groups may be partly or totally fluorinated.

Examples of the most particularly preferred groups $R^1$ are hydrogen, fluorine, chlorine, bromine, methyl, ethyl, isopropyl, trifluoromethyl, ethynyl, methoxy, cyclopentyloxy and cyano, particularly chlorine and methyl.

The group $R^3$ preferably denotes fluorine, chlorine, bromine, $C_{1-6}$-alkyl, $C_{2-6}$-alkynyl, $C_{2-6}$-alkenyl, $C_{3-7}$-cycloalkyl, $C_{3-7}$-cycloalkyl-methyl, $C_{5-7}$-cycloalkenyl, $C_{3-7}$-cycloalkenyl-methyl, aryl, heteroaryl, $C_{1-4}$-alkylcarbonyl, aminocarbonyl, $C_{1-4}$-alkylaminocarbonyl, di-($C_{1-3}$-alkyl)aminocarbonyl, $C_{1-4}$-alkoxycarbonyl, di-($C_{1-3}$-alkyl)amino, pyrrolidin-1-yl, piperidin-1-yl, morpholin-4-yl, $C_{1-4}$-alkylcarbonylamino, $C_{1-6}$-alkoxy, $C_{3-7}$-cycloalkyloxy, $C_{5-7}$-cycloalkenyloxy, aryloxy, heteroaryloxy, $C_{1-4}$-alkylsulphanyl, $C_{1-4}$-alkylsulphonyl, $C_{3-7}$-cycloalkylsulphanyl, $C_{3-7}$-cycloalkylsulphonyl, $C_{5-7}$-cycloalkenylsulphanyl, $C_{5-7}$-cycloalkenylsulphonyl, hydroxy and cyano, while alkyl, alkenyl, alkynyl, cycloalkyl and cycloalkenyl groups may be partly or totally fluorinated or mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, while the terms aryl and heteroaryl are as hereinbefore defined and aryl and heteroaryl groups may be mono- or disubstituted independently of one another by identical or different groups L.

If the group $R^3$ denotes a cycloalkyl or cycloalkenyl group wherein one or two methylene groups are replaced independently of one another by O, S, CO, SO or $SO_2$, preferred definitions of the group $R^3$ are selected from among tetrahydrofuranyl, tetrahydrofuranonyl, tetrahydrothienyl, tetrahydropyranyl, tetrahydropyranonyl, dioxanyl and trioxanyl.

If the group $R^3$ denotes an N-heterocycloalkyl group wherein a methylene group is replaced by CO or $SO_2$, preferred meanings of the group $R^3$ are selected from among pyrrolidinone, piperidinone, piperazinone and morpholinone.

Particularly preferred definitions of $R^3$ are $C_{1-6}$-alkyl, $C_{2-6}$-alkynyl, $C_{1-4}$-alkyloxy, $C_{3-7}$-cycloalkyl, $C_{3-7}$-cycloalkyloxy and hydroxy, while in the cycloalkyl groups one or two methylene units may be replaced independently of one another by O or CO and alkyl groups may be partly or totally fluorinated.

Most particularly preferred groups $R^3$ are methyl, ethyl, ethynyl, isopropyl, methoxy, ethoxy, isopropyloxy, difluoromethoxy, cyclopentyloxy, tetrahydro-furan-3-yloxy and hydroxy.

A selection of the most particularly preferred examples of $R^3$ includes methyl, ethyl, isopropyl, ethynyl, methoxy, ethoxy, cyclopentyloxy and hydroxy.

According to a preferred alternative embodiment of the present invention $R^3$ denotes $C_{2-6}$-alkynyl, particularly ethynyl.

The group X preferably denotes hydrogen, $C_{1-6}$-alkyl, $C_{2-6}$-alkynyl, $C_{2-6}$-alkenyl, $C_{3-7}$-cycloalkyl-$C_{1-3}$-alkyl, $C_{5-7}$-cycloalkenyl-$C_{1-3}$-alkyl, aryl, aryl-$C_{1-3}$-alkyl, heteroaryl, heteroaryl-$C_{1-3}$-alkyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, $C_{1-4}$-alkoxycarbonyl, $C_{1-4}$-alkylcarbonylamino-$C_{1-3}$-alkyl, N-($C_{1-4}$-alkylcarbonyl)-N-($C_{1-3}$-alkyl)-amino-$C_{1-3}$-alkyl, arylcarbonylamino-$C_{1-3}$-alkyl, $C_{1-6}$-alkoxy-$C_{1-3}$-alkyl, $C_{3-7}$-cycloalkyloxy-$C_{1-3}$-alkyl, $C_{5-7}$-cycloalkenyloxy-$C_{1-3}$-alkyl, aryloxy-$C_{1-3}$-alkyl, heteroaryloxy-$C_{1-3}$-alkyl, $C_{1-4}$-alkylcarbonylsulphanyl-$C_{1-3}$-alkyl or $C_{1-4}$-alkylsulphanyl-$C_{1-3}$-alkyl, while alkyl, alkenyl, alkynyl, cycloalkyl and cycloalkenyl groups may be partly or totally fluorinated or mono- or disubstituted by identical or different substituents selected from chlorine, cyano, hydroxy, mercapto, $C_{1-3}$-alkoxy and $C_{1-3}$-alkyl, and in the above-mentioned cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, and the terms aryl and heteroaryl are as hereinbefore defined and aryl and heteroaryl groups may be mono- or disubstituted independently of one another by identical or different groups L, and X representing hydroxymethyl is excluded.

According to a first embodiment X preferably denotes hydrogen, cyano, $C_{1-6}$-alkyl, $C_{2-6}$-alkynyl, $C_{2-6}$-alkenyl, $C_{3-7}$-cycloalkyl-$C_{1-3}$-alkyl, $C_{5-7}$-cycloalkenyl-$C_{1-3}$-alkyl, aryl-$C_{1-3}$-alkyl, heteroaryl-$C_{1-3}$-alkyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, $C_{1-4}$-alkylcarbonyl, $C_{1-4}$-alkoxycarbonyl, $C_{1-4}$-alkylcarbonylamino-$C_{1-3}$-alkyl, N-($C_{1-4}$-alkylcarbonyl)-N-($C_{1-3}$-alkyl)-amino-$C_{1-3}$-alkyl, arylcarbonylamino-$C_{1-3}$-alkyl, $C_{1-6}$-alkoxy-$C_{2-3}$-alkyl, $C_{3-7}$-cycloalkyloxy-$C_{2-3}$-alkyl, $C_{5-7}$-cycloalkenyloxy-$C_{2-3}$-alkyl, aryloxy-$C_{2-3}$-alkyl, heteroaryloxy-$C_{2-3}$-alkyl and $C_{1-4}$-alkylsulphanyl-$C_{2-3}$-alkyl, while alkoxy, alkenyl, alkynyl, cycloalkyl and cycloalkenyl groups may be partly or totally fluorinated or mono- or disubstituted by identical or different substituents selected from chlorine, cyano, hydroxy, mercapto, $C_{1-3}$-alkoxy and $C_{1-3}$-alkyl, and methyl groups may be partly or totally fluorinated or monosubstituted by chlorine, and alkyl groups with 2 or more C atoms may be partly or totally fluorinated or mono- or disubstituted by identical or different substituents selected from chlorine, cyano, hydroxy, mercapto and $C_{1-3}$-alkoxy, while in the above-mentioned cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, and the terms aryl and heteroaryl are as hereinbefore defined and aryl and heteroaryl groups may be mono- or disubstituted independently of one another by identical or different groups L.

If the group X denotes a cycloalkyl or cycloalkenyl group wherein one or two methylene groups are replaced independently of one another by O, S, CO, SO or $SO_2$, preferred definitions of the group X are selected from among tetrahydrofuranyl, tetrahydrofuranonyl, tetrahydrothienyl, tetrahydropyranyl, tetrahydropyranonyl, dioxanyl and trioxanyl.

If the group X denotes an N-heterocycloalkyl group wherein a methylene group is replaced by CO or $SO_2$, preferred meanings of the group X are selected from among pyrrolidinone, piperidinone, piperazinone and morpholinone.

Particularly preferred radicals of the group X are hydrogen, cyano, $C_{1-6}$-alkyl, $C_{2-6}$-alkynyl, $C_{2-6}$-alkenyl, $C_{1-4}$-alkylcarbonyl, $C_{1-4}$-alkoxycarbonyl, aminocarbonyl, $C_{1-4}$-alkylaminocarbonyl, di-($C_{1-4}$-alkyl)aminocarbonyl, $C_{1-4}$-alkylcarbonylamino-$C_{1-3}$-alkyl, while alkyl groups may be mono- or polyfluorinated or monosubstituted by chlorine or cyano and X representing alkyl with 2 or more C atoms may have a hydroxy substituent.

Most particularly preferred groups X are hydrogen, cyano, methyl, ethyl, propyl, fluoromethyl, trifluoromethyl, chloromethyl, cyanomethyl, 1-hydroxyethyl, 1-hydroxy-1-methylethyl, 2-hydroxyethyl, prop-2-enyl, prop-2-ynyl, methylcarbonyl, aminocarbonyl, methylaminocarbonyl, methylaminocarbonylmethyl, methoxycarbonyl and acetylaminomethyl.

A selection of the most particularly preferred groups X includes methyl, ethyl, fluoromethyl, chloromethyl, cyanomethyl and acetylaminomethyl, particularly methyl, fluoromethyl and cyanomethyl.

According to a second embodiment X preferably denotes $C_{1-6}$-alkoxy-methyl, $C_{3-7}$-cycloalkyloxy-methyl, $C_{5-7}$-cycloalkenyloxy-methyl, aryloxy-methyl or heteroaryloxy-methyl, while the above-mentioned alkoxy, cycloalkyl and cycloalkenyl groups may be partly or totally fluorinated or mono- or disubstituted by identical or different substituents selected from chlorine, hydroxy, $C_{1-3}$-alkoxy and $C_{1-3}$-alkyl, and while in the above-mentioned cycloalkyl and cycloalkenyl groups one or two methylene groups may be replaced independently of one another by O, S, CO, SO or $SO_2$, and ther terms aryl and heteroaryl are as hereinbefore defined and aryl and heteroaryl groups may be mono- or disubstituted independently of one another by identical or different groups L.

Preferred meanings of the group X according to this embodiment are $C_{1-4}$-alkyloxymethyl, $C_{3-7}$-cycloalkyloxymethyl and aryloxymethyl, while the term aryl denotes a phenyl or naphthyl group, particularly phenyl, which may be mono- or disubstituted by identical or different substituents L.

Particularly preferred meanings of the group X are phenoxymethyl and methoxymethyl, the phenyl ring being unsubstituted or mono- or disubstituted by identical or different substituents L, particularly methoxymethyl.

According to a third embodiment X preferably denotes mercaptomethyl, $C_{1-6}$-alkylsulphanylmethyl or $C_{1-6}$-alkylcarbonylsulphanylmethyl, while the above-mentioned alkyl groups may be partly or totally fluorinated or mono- or disubstituted by identical or different substituents selected from chlorine, hydroxy, $C_{1-3}$-alkoxy and $C_{1-3}$-alkyl.

Preferred meanings of the group X according to this embodiment are mercaptomethyl and $C_{1-4}$-alkylsulphanylmethyl.

Particularly preferred meanings of the group X are mercaptomethyl and methylsulphanylmethyl.

According to a fourth embodiment X preferably denotes chloromethyl, bromomethyl, iodomethyl, $C_{1-6}$-alkylsulphonyloxymethyl, arylsulphonyloxymethyl or aryl-$C_{1-3}$-alkylsulphonyloxymethyl, while the above-mentioned alkyl groups may be partly or totally fluorinated or mono- or dichlorinated and the above-mentioned aryl groups may be mono- or disubstituted by identical or different groups L, while L is preferably selected from among fluorine, chlorine, bromine, iodine, $C_{1-3}$-alkyl, difluoromethyl, trifluoromethyl and cyano.

The compounds according to this fourth embodiment are particularly suitable by virtue of their pharmaceutical activity as described above as intermediate products in the synthesis of compounds with an SGLT, preferably SGLT2 inhibiting effect, particularly in the synthesis of other compounds according to the invention.

Particularly preferred groups X according to this embodiment are bromomethyl, iodomethyl, $C_{1-4}$-alkylsulphonyloxymethyl, phenylsulphonyloxymethyl or phenylmethylsulphonyloxymethyl, while the above-mentioned alkyl groups may be partly or totally fluorinated and the above-mentioned phenyl groups may be mono- or disubstituted by identical or different groups L, while L is preferably selected from among fluorine, chlorine, bromine and methyl.

Most particularly preferably, X here denotes bromomethyl or iodomethyl.

If there are cycloalkyl or cycloalkenyl rings wherein two methylene groups are replaced by O or S or by CO, SO or $SO_2$ in the radicals or groups X, $R^1$ or $R^3$, these methylene groups are preferably not joined together directly. However, if two methylene groups are replaced by O and CO, they may be joined together directly, so that a —O—CO— or —CO—O— group is formed. If X, $R^1$ or $R^3$ is a cycloalkyl or cycloalkenyl group with one or two methylene groups replaced according to the invention, the relevant group X, $R^1$ or $R^3$ preferably denotes a cycloalkyl or cycloalkenyl group wherein a methylene group is replaced by O, S, CO, SO or $SO_2$ or an ethylene group is replaced by —O—CO— or —CO—O—.

Some meanings of other groups and substituents will now be given, which are to be regarded as preferred according to general formula I, formulae I.1 and I.2 and the embodiments described hereinbefore:

Preferred meanings of the group $R^2$ are hydrogen, fluorine, chlorine, bromine, methyl, hydroxy, methoxy, ethoxy, trifluoromethoxy, cyano, nitro and methyl substituted by 1 to 3 fluorine atoms.

Particularly preferred meanings of the group $R^2$ are hydrogen, fluorine, hydroxy, methoxy, ethoxy and methyl, particularly hydrogen and methyl.

If $R^1$ and $R^2$ are bound to two C atoms of the phenyl ring which are adjacent to one another, $R^1$ and $R^2$ may be joined together in such a way that $R^1$ and $R^2$ together preferably form a $C_{3-4}$ bridge, wherein one or two methylene units may be replaced independently of one another by O, $NR^N$ or CO. Preferably, the groups $R^1$ and $R^2$ joined to one another, together with the phenyl ring by which they are joined, form a bicyclic ring system selected from among dihydroindane, dihydroindole, dihydrobenzofuran, tetrahydroquinoline, tetrahydroquinolinone, tetrahydroisoquinoline, tetrahydroisoquinolinone and tetrahydronaphthalene.

Preferred meanings of the group $R^4$ are hydrogen and fluorine, particularly hydrogen.

If $R^3$ and $R^4$ are bound to two C atoms of the phenyl ring which are immediately adjacent to one another, $R^3$ and $R^4$ may be joined together in such a way that $R^1$ and $R^2$ together preferably form a $C_{3-4}$ bridge, wherein one or two methylene units may be replaced independently of one another by O, $NR^N$ or CO. Preferably the interconnected groups $R^3$ and $R^4$ together with the phenyl ring by which they are joined form a bicyclic ring system selected from among dihydroindane, dihydroindole, dihydrobenzofuran, tetrahydroquinoline, tetrahydroquinolinone, tetrahydroisoquinoline, tetrahydroisoquinolinone and tetrahydronaphthalene.

Preferred meanings of the group $R^5$ are hydrogen and fluorine, particularly hydrogen.

Preferred meanings of the group Z are oxygen and methylene, particularly methylene.

The substituents $R^{7a}$, $R^{7b}$, $R^{7c}$ preferably represent, independently of one another, hydrogen, ($C_{1-8}$-alkyl)oxycarbonyl, ($C_{1-8}$-alkyl)carbonyl, benzoyl, particularly hydrogen or ($C_{1-6}$-alkyl)oxycarbonyl, ($C_{1-8}$-alkyl)carbonyl, particularly preferably hydrogen, methoxycarbonyl, ethoxycarbonyl, methylcarbonyl or ethylcarbonyl. Most particularly preferably $R^{7a}$, $R^{7b}$ and $R^{7c}$ denote hydrogen.

The compounds of formula I wherein $R^{7a}$, $R^{7b}$ and $R^{7c}$ have a meaning according to the invention other than hydrogen, for example $C_{1-8}$-alkylcarbonyl, are preferably suitable as intermediate products in the synthesis of compounds of formula I wherein $R^{7a}$, $R^{7b}$ and $R^{7c}$ denote hydrogen.

The substituents L are preferably selected independently of one another from the group consisting of fluorine, chlorine, bromine, $C_{1-3}$-alkyl, difluoromethyl, trifluoromethyl, $C_{1-3}$-alkoxy, difluoromethoxy, trifluoromethoxy and cyano, particularly preferably from the group consisting of fluorine, chlorine, methyl, trifluoromethyl, methoxy and difluoromethoxy.

Particularly preferred compounds of general formula I are selected from among the formulae I.2a to I.2d, particularly formula I.2c:

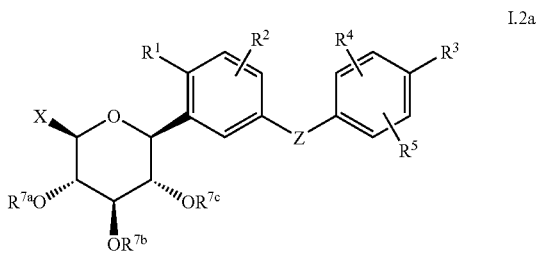

I.2a

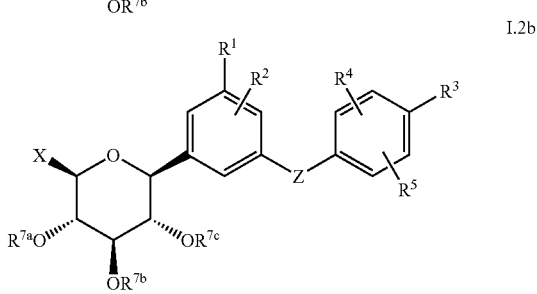

I.2b

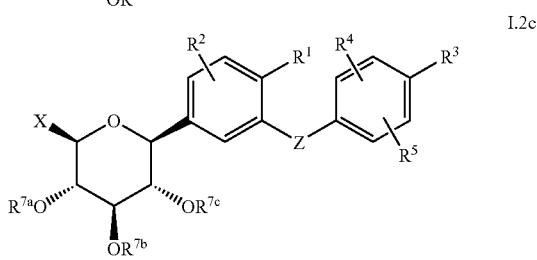

I.2c

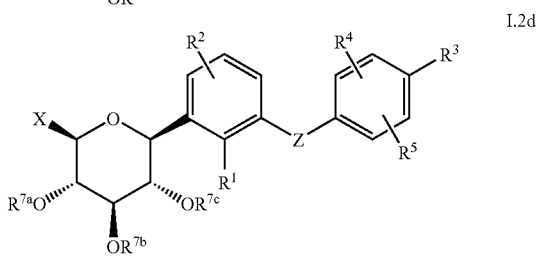

I.2d wherein $R^1$ to $R^5$, X, Z, $R^{7a}$, $R^{7b}$, $R^{7c}$ are as hereinbefore defined Most particularly preferred are those compounds of formulae I.2a, I.2b, I.2c and I.2d, particularly formula I.2c, wherein the groups $R^1$ to $R^5$, X, Z, $R^{7a}$, $R^{7b}$, $R^{7c}$ have the meanings given hereinbefore as being preferred, particularly wherein $R^1$ denotes hydrogen, fluorine, chlorine, bromine, $C_{1-6}$alkyl, $C_{2-6}$-alkynyl, $C_{2-6}$-alkenyl, $C_{3-7}$-cycloalkyl, $C_{5-7}$-cycloalkenyl, $C_{1-6}$-alkyloxy, $C_{3-7}$-cycloalkyloxy or cyano, while in cycloalkyl and cycloalkenyl groups one or two methylene units may be replaced independently of one another by O or CO and alkyl, alkenyl and alkynyl groups may be partly or totally fluorinated, particularly preferably denotes hydrogen, fluorine, chlorine, bromine, methyl, ethyl, isopropyl, trifluoromethyl, ethynyl, methoxy, cyclopentyloxy or cyano, particularly chlorine, methyl or ethynyl, and $R^3$ denotes $C_{1-6}$-alkyl, $C_{2-6}$-alkynyl, $C_{1-4}$-alkyloxy, $C_{3-7}$-cycloalkyl, $C_{3-7}$-cycloalkyloxy or hydroxy, particularly $C_{2-6}$-alkynyl, while in the cycloalkyl groups one or two methylene units may be replaced independently of one another by O or CO and alkyl groups may be partly or totally fluorinated, particularly preferably denotes methyl, ethyl, ethynyl, isopropyl, methoxy, ethoxy, isopropyloxy, difluoromethoxy, cyclopentyloxy, tetrahydro-furan-3-yloxy or hydroxy, particularly ethynyl, and X according to a first embodiment denotes hydrogen, cyano, $C_{1-6}$-alkyl, $C_{2-6}$-alkynyl, $C_{2-6}$-alkenyl, $C_{1-4}$-alkylcarbonyl, $C_{1-4}$-alkoxycarbonyl, aminocarbonyl, $C_{1-4}$-alkylaminocarbonyl, di-($C_{1-4}$-alkyl)aminocarbonyl, $C_{1-4}$-alkylcarbonylamino-$C_{1-3}$-alkyl, while alkyl groups may be mono- or polyfluorinated or monosubstituted by chlorine or cyano and X representing alkyl with 2 or more C atoms may have a hydroxy substituent; particularly preferably hydrogen, cyano, methyl, ethyl, propyl, fluoromethyl, trifluoromethyl, chloromethyl, cyanomethyl, 1-hydroxyethyl, 1-hydroxy-1-methylethyl, 2-hydroxyethyl, prop-2-enyl, prop-2-inyl, methylcarbonyl, aminocarbonyl, methylaminocarbonyl, methylaminocarbonylmethyl, methoxycarbonyl or acetylaminomethyl, particularly methyl, fluoromethyl or cyanomethyl; or according to a second embodiment denotes $C_{1-4}$-alkyloxymethyl, $C_{3-7}$-cycloalkyloxymethyl or aryloxymethyl, while by aryl is meant a phenyl or naphthyl group, particularly phenyl, which may be mono- or disubstituted by identical or different substituents L, particularly preferably denotes phenoxymethyl or methoxymethyl, or according to a third embodiment denotes mercaptomethyl or $C_{1-4}$-alkylsulphanylmethyl, particularly preferably denotes mercaptomethyl or methylsulphanylmethyl, or according to a fourth embodiment denotes chloromethyl, bromomethyl, iodomethyl, $C_{1-6}$-alkylsulphonyloxymethyl, arylsulphonyloxymethyl or aryl-$C_{1-3}$-alkyl-sulphonyloxymethyl, while alkyl groups may be partly or totally fluorinated or mono- or dichlorinated and aryl groups may be mono- or disubstituted by identical or different groups L, while L is preferably selected from among fluorine, chlorine, bromine, iodine, $C_{1-3}$-alkyl, difluoromethyl, trifluoromethyl and cyano, particularly preferably X denotes bromomethyl, iodomethyl, $C_{1-4}$-alkylsulphonyloxy-methyl, phenylsulphonyloxymethyl or phenylmethylsulphonyloxymethyl, while alkyl groups may be partly or totally fluorinated and phenyl groups may be mono- or disubstituted by identical or different groups L, while L is preferably selected from among fluorine, chlorine, bromine and methyl; and $R^2$ denotes hydrogen, fluorine, chlorine, bromine, methyl, hydroxy, methoxy, ethoxy, trifluoromethoxy, cyano, nitro or methyl substituted by 1 to 3 fluorine atoms, particularly preferably denotes hydrogen, fluorine, hydroxy, methoxy, ethoxy or methyl, particularly hydrogen or methyl, and $R^4$ denotes hydrogen or fluorine, particularly hydrogen, and $R^5$ denotes hydrogen or fluorine, particularly hydrogen, and Z denotes oxygen or methylene, particularly methylene, and $R^{7a}$, $R^{7b}$, $R^{7c}$ independently of one another represent hydrogen, ($C_{1-8}$-alkyl)oxycarbonyl, ($C_{1-18}$-alkyl)carbonyl or benzoyl, particularly hydrogen or ($C_{1-6}$alkyl)oxycarbonyl, ($C_{1-8}$-alkyl)carbonyl, particularly preferably hydrogen, methoxycarbonyl, ethoxycarbonyl, methylcarbonyl or ethylcarbonyl, most particularly preferably hydrogen, and L independently of one another represent fluorine, chlorine, bromine, $C_{1-3}$-alkyl, difluoromethyl, trifluoromethyl, $C_{1-3}$-alkoxy, difluoromethoxy, trifluoromethoxy and cyano, including the tautomers, the stereoisomers, the mixtures thereof and the salts thereof, particularly the physiologically acceptable salts thereof.

According to a variant of the above-mentioned embodiments, those compounds wherein the phenyl group which carries the substituent $R^3$ comprises at least one other substituent $R^4$ and/or $R^5$ which is other than hydrogen are also preferred. According to this variant those compounds which comprise a substituent $R^4$ representing fluorine are also preferred.

The phenyl group which carries the substituent $R^3$ is preferably at most difluorinated.

Particularly preferred compounds of general formula I are selected from among:

(a) 1-chloro-2-(4-methoxy-benzyl)-4-(6-desoxy-6-fluoro-β-D-glucopyranos-1-yl)-benzene, (b) 1-chloro-2-(4-methoxy-benzyl)-4-(6-desoxy-6-chloro-β-D-glucopyranos-1-yl)-benzene, (c) 1-chloro-2-(4-methoxy-benzyl)-4-(6-desoxy-6-acetylamino-β-D-glucopyranos-1-yl)-benzene, (d) 1-chloro-2-(4-methoxy-benzyl)-4-(6-O-phenyl-β-D-glucopyranos-1-yl)-benzene, (e) 1-chloro-2-(4-methoxy-benzyl)-4-(6-desoxy-β-D-glucopyranos-1-yl)-benzene, (f) 1-chloro-2-(4-methoxy-benzyl)-4-(6-cyano-6-desoxy-β-D-glucopyranos-1-yl)-benzene, (g) 1-chloro-2-(4-methoxy-benzyl)-4-(6-desoxy-6-mercapto-β-D-glucopyranos-1-yl)-benzene, (h) 1-chloro-2-(4-methoxy-benzyl)-4-(6-desoxy-6-methylsulphanyl-β-D-glucopyranos-1-yl)-benzene, (i) 1-chloro-2-(4-ethynyl-benzyl)-4-(6-cyano-6-desoxy-β-D-glucopyranos-1-yl)-benzene, (j) 1-bromo-2-(4-ethynyl-benzyl)-4-(6-cyano-6-desoxy-β-D-glucopyranos-1-yl)-benzene, (k) 1-methyl-2-(4-ethynyl-benzyl)-4-(6-cyano-6-desoxy-β-D-glucopyranos-1-yl)-benzene, (l) 1-methoxy-2-(4-ethynyl-benzyl)-4-(6-cyano-6-desoxy-β-D-glucopyranos-1-yl)-benzene, (m) 1-chloro-2-(4-ethynyl-benzyl)-4-(6-O-methyl-β-D-glucopyranos-1-yl)-benzene, (n) 1-chloro-2-(4-methoxy-benzyl)-4-(6-O-methyl-β-D-glucopyranos-1-yl)-benzene, including the tautomers, the stereoisomers and the mixtures thereof.

Some terms used above and hereinafter to describe the compounds according to the invention will now be defined more closely.

The term halogen denotes an atom selected from the group consisting of F, Cl, Br and I, particularly F, Cl and Br.

The term $C_{1-n}$-alkyl, wherein n may have a value of 1 to 18, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{2-n}$-alkynyl, wherein n has a value of 3 to 6, denotes a branched or unbranched hydrocarbon group with 2 to n C atoms and a C≡C triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 4-methyl-2-pentynyl etc. Unless stated otherwise, alkynyl groups are linked to the rest of the molecule via the C atom in position 1. Therefore, terms such as 1-propynyl, 2-propynyl, 1-butynyl, etc. are equivalent to the terms 1-propyn-1-yl, 2-propyn-1-yl, 1-butyn-1-yl, etc. This also applies analogously to $C_{2-n}$-alkenyl groups.

The term $C_{1-n}$-alkoxy or $C_{1-n}$-alkyloxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{1-n}$-alkylcarbonyl denotes a $C_{1-n}$-alkyl-C(=O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, decalin, bicyclo[3.2.1.]octyl, spiro[4.5]decyl, norpinyl, norbonyl, norcaryl, adamantyl, etc. Preferably the term $C_{3-7}$-cycloalkyl denotes saturated monocyclic groups.

The term $C_{3-n}$-cycloalkyloxy denotes a $C_{3-n}$-cycloalkyl-O group, wherein $C_{3-n}$-cycloalkyl is as hereinbefore defined. Examples of such groups include cyclopropyloxy, cyclobutyloxy, cyclopentyloxy, cyclohexyloxy, cycloheptyloxy, etc.

The term $C_{5-n}$-cycloalkenyl denotes a $C_{5-n}$-cycloalkyl group which is as hereinbefore defined and additionally comprises at least one unsaturated C=C double bond.

The term $C_{3-n}$-cycloalkylcarbonyl denotes a $C_{3-n}$-cycloalkyl-C(=O) group wherein $C_{3-n}$-cycloalkyl is as hereinbefore defined.

The term tri-($C_{1-4}$-alkyl)silyl comprises silyl groups which comprises identical alkyl groups or two or three different alkyl groups.

The term di-($C_{1-3}$-alkyl)amino comprises amino groups which have identical alkyl groups or two different alkyl groups.

The term N-heterocycloalkyl denotes a saturated carbocyclic ring which comprises an imino group in the ring, and which may additionally comprise another optionally substituted imino group or an O or S atom in the ring. By an imino group is meant the group —NH—. Examples of such N-heterocycloalkyl groups are pyrrolidine, piperidine, piperazine, N-alkyl-piperazine and morpholine.

If alkyl radicals occurring in groups, for example in X, $R^1$ or $R^3$, may be substituted, e.g. fluorinated, this encompasses not only alkyl radicals in the groups which represent alkyl directly but also in other definitions which include alkyl groups, such as for example alkoxy, alkylcarbonyl, alkoxyalkyl, etc. Thus, for example X, $R^1$ and $R^3$ representing alkoxy, wherein the alkyl groups may be partly or totally fluorinated, also include difluoromethoxy and trifluoromethoxy.

The style used above and hereinafter, in which a bond of a substituent in a phenyl group is shown towards the centre of the phenyl ring, denotes, unless otherwise stated, that this substituent may be bound to any free position of the phenyl ring bearing an H atom.

The compounds according to the invention may be obtained using methods of synthesis known in principle. Preferably the compounds are obtained by the following methods according to the invention which are described in more detail hereinafter.

The D-xylose derivatives described below may be obtained from D-glucose by replacement of the 6-hydroxy group or suitable derivatisation of the 6-hydroxy group and subsequent substitution with the desired group. Such transformations are within the general expertise of the skilled man or are at least known from the specialist literature as methods used in organic synthesis and may readily be carried out by the skilled man in respect of the compounds according to the invention.

In order to prepare compounds of general formula I, according to to process a) according to the invention, a compound of general formula II

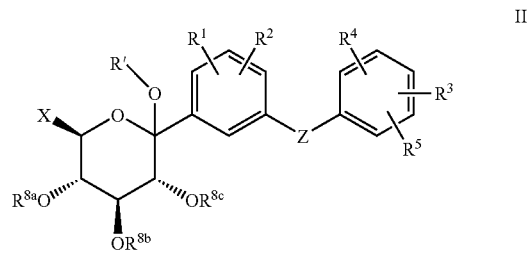

wherein X, Z and R', $R^1$ to $R^5$ are as hereinbefore defined and $R^{8a}$, $R^{8b}$ and $R^{8c}$ are as hereinbefore defined and independently of one another represent acetyl, pivaloyl, benzoyl, tert-butoxycarbonyl, benzyloxycarbonyl, trialkylsilyl, benzyl or substituted benzyl, for example, is reacted with a reducing agent in the presence of an acid.

Suitable reducing agents for the reaction include for example silanes, such as triethyl, tripropyl, triisopropyl or diphenyl silane, sodium borohydride, sodium cyanoborohydride, zinc borohydride, borane, lithium aluminium hydride, diisobutylaluminium hydride or samarium iodide. The reductions are preferably carried out in the presence of a suitable acid, such as e.g. hydrochloric acid, toluenesulphonic acid, trifluoroacetic acid, acetic acid, boron trifluoride etherate, trimethylsilyl triflate, titanium tetrachloride, tin tetrachloride, scandium triflate or zinc iodide. Depending on the reducing agent and the acid the reaction may be carried out in a solvent, such as for example methylene chloride, chloroform, acetonitrile, toluene, hexane, diethyl ether, tetrahydrofuran, dioxane, ethanol, water or mixtures thereof at temperatures between −60° C. and 120° C. A particularly suitable combination of reagents consists for example of triethylsilane and boron trifluoride etherate, which is expediently used in acetonitrile or dichloromethane at temperatures from −60° C. to 60° C. In addition, hydrogen may be used for the transformation described, in the presence of a transition metal catalyst such as e.g. palladium on charcoal or Raney nickel, in solvents such as tetrahydrofuran, ethyl acetate, methanol, ethanol, water or acetic acid.

Alternatively, in order to prepare compounds of general formula I according to method b) of the invention, in a compound of general formula III

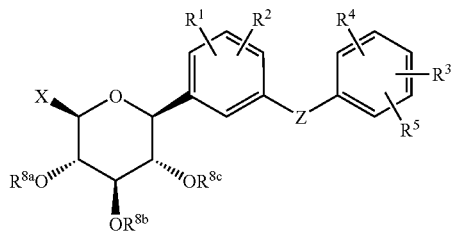

III wherein X, Z and $R^1$ to $R^5$ are as hereinbefore defined and $R^8$, to $R^{8c}$ represent one of the protective groups defined hereinbefore, such as e.g. an acyl, arylmethyl, acetal, ketal or silyl group, the protective groups are cleaved.

Any acyl, acetal or ketal protecting group used is cleaved hydrolytically, for example, in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or aprotically, e.g. in the presence of iodotrimethylsilane, at temperatures between 0 and 120° C., preferably at temperatures between 10 and 100° C. An acyl group may also be cleaved in the presence of an alkali metal base such as lithium hydroxide, sodium hydroxide or potassium hydroxide. A trifluoroacetyl group is preferably cleaved by treatment with an acid such as hydrochloric acid, optionally in the presence of a solvent such as acetic acid, at temperatures between 50 and 120° C. or by treatment with sodium hydroxide solution, optionally in the presence of a solvent such as tetrahydrofuran or methanol, at temperatures between 0 and 50° C.

A trimethylsilyl group is cleaved for example in water, an aqueous solvent mixture or a lower alcohol such as methanol or ethanol in the presence of a base such as lithium hydroxide, sodium hydroxide, potassium carbonate or sodium methoxide. In aqueous or alcoholic solvents, acids, such as e.g. hydrochloric acid, trifluoroacetic acid or acetic acid are also suitable, for example. Fluoride reagents, such as e.g. tetrabutylammonium fluoride, are also suitable for cleaving in organic solvents, such as for example diethyl ether, tetrahydrofuran or dichloromethane.

A benzyl, methoxybenzyl or benzyloxycarbonyl group is advantageously cleaved hydrogenolytically, e.g. with hydrogen in the presence of a catalyst such as palladium/charcoal, in a suitable solvent such as methanol, ethanol, ethyl acetate or glacial acetic acid, optionally with the addition of an acid such as hydrochloric acid, at temperatures between 0 and 100° C., but preferably at ambient temperature between 20 and 60° C., and under a hydrogen pressure of 1 to 7 bar, but preferably from 3 to 5 bar. However, a 2,4-dimethoxybenzyl group is preferably cleaved in trifluoroacetic acid in the presence of anisole.

A tert.-butyl or tert.-butyloxycarbonyl group is preferably cleaved by treatment with an acid such as trifluoroacetic acid or hydrochloric acid or by treatment with iodotrimethylsilane, optionally using a solvent such as methylene chloride, dioxane, methanol or diethyl ether.

In the reactions described hereinbefore, any reactive groups present such as ethynyl, hydroxy, amino, alkylamino or imino groups may be protected during the reaction by conventional protecting groups which are cleaved again after the reaction, e.g. as described above.

For example, a protecting group for an ethynyl group may be a trimethylsilyl or triisopropyl group. The 2-hydroxyisoprop-2-yl group may also be used as a protective group.

For example, a protecting group for a hydroxy group may be a trimethylsilyl, acetyl, trityl, benzyl or tetrahydropyranyl group.

Examples of protecting groups for an amino, alkylamino or imino group include the formyl, acetyl, trifluoroacetyl, ethoxycarbonyl, tert.-butoxycarbonyl, benzyloxycarbonyl, benzyl, methoxybenzyl or 2,4-dimethoxybenzyl group.

Furthermore, the compounds of general formula I thus obtained may be selectively derivatised at a hydroxy group or the hydroxy group itself may be substituted (see Examples VII, VIII, 1, 2, 4, 5, 6).

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, the compounds obtained may be converted into mixtures, for example 1:1 or 1:2 mixtures with amino acids, particularly with alpha-amino acids such as proline or phenylalanine, which may have particularly favourable properties such as a high crystallinity.

The compounds of general formulae II and III used as starting materials are partly known from the literature or may be obtained by methods known from the literature and also analogously to the methods described in the Examples, optionally with the additional inclusion of protecting groups.

The compounds according to the invention may advantageously also be obtained by the methods described in the following Examples, which may also be combined with methods known to the skilled man from the literature, for example, particularly the methods described in WO 98/31697, WO 01/27128, WO 02/083066, WO 03/099836, WO 04/063209 and WO 04/76470.

As already mentioned hereinbefore, the compounds of general formula I according to the invention and the physiologically acceptable salts thereof have valuable pharmacological properties, particularly an inhibitory effect on the sodium-dependent glucose cotransporter SGLT, preferably SGLT2.

The biological properties of the new compounds may be investigated as follows:

The ability of the substances to inhibit the SGLT-2 activity may be demonstrated in a test set-up in which a CHO-K1 cell line (ATCC No. CCL 61) or alternatively an HEK293 cell line (ATCC No. CRL-1573), which is stably transfected with an expression vector pZeoSV (Invitrogen, EMBL accession number L36849), which contains the cDNA for the coding sequence of the human sodium glucose cotransporter 2 (Genbank Acc. No. NM_003041) (CHO-hSGLT2 or HEK-hSGLT2). These cell lines transport $^{14}$C-labelled alpha-methyl-glucopyranoside ($^{14}$C-AMG, Amersham) into the interior of the cell in sodium-dependent manner.

The SGLT-2 assay is carried out as follows: CHO-hSGLT2 cells are cultivated in Ham's F12 Medium (BioWhittaker) with 10% foetal calf serum and 250 µg/ml zeocin (Invitrogen), and HEK293-hSGLT2 cells are cultivated in DMEM medium with 10% foetal calf serum and 250 µg/ml zeocin (Invitrogen).

The cells are detached from the culture flasks by washing twice with PBS and subsequently treating with trypsin/EDTA. After the addition of cell culture medium the cells are centrifuged, resuspended in culture medium and counted in a Casy cell counter. Then 40,000 cells per well are seeded into a white, 96-well plate coated with poly-D-lysine and incubated overnight at 37° C., 5% $CO_2$. The cells are washed twice with 250 µl of assay buffer (Hanks Balanced Salt Solution, 137 mM NaCl, 5.4 mM KCl, 2.8 mM $CaCl_2$, 1.2 mM $MgSO_4$ and 10 mM HEPES (pH7.4), 50 µg/ml of gentamycin). 300 µl of assay buffer and 5 µl of test compound are then added to each well and the plate is incubated for a further 15 minutes in the incubator. 5 µl of 10% DMSO are used as the negative control. The reaction is started by adding 5 µl of $^{14}$C-AMG (0.05 µCi) to each well. After 2 hours' incubation at 37° C., 5% $CO_2$, the cells are washed again with 300 µl of PBS (20° C.) and then lysed by the addition of 25 µl of 0.1 N NaOH (5 min. at 37° C.). 200 µl of MicroScint20 (Packard) are added to each well and incubation is continued for a further 20 min at 37° C. After this incubation the radioactivity of the $^{14}$C-AMG absorbed is measured in a Topcount (Packard) using a $^{14}$C scintillation program.

To determine the selectivity with respect to human SGLT1 an analogous test is set up in which the cDNA for hSGLT1 (Genbank Acc. No. NM000343) instead of hSGLT2 cDNA is expressed in CHO-K1 or HEK293 cells.

Alternatively, measurement of the cellular membrane potential for hSGLT1 and hSGLT2 may also be used for the biological testing of substances. The cell models described earlier may be used for this. For the test, 10,000 cells per well of a black 384-well plate with a transparent base coated with poly-D-lysine are seeded in culture medium and incubated for 16 hours at 37° C., 5% $CO_2$. Then the cells are washed twice with glucose-free HBSS buffer (12.67 mol/l $CaCl_2$, 4.93 mmol/l $MgCl_2$, 4.07 mmol/l $MgSO_4$, 4.41 mmol/l $KH_2PO_4$; pH 7.4) and covered with 20 µl HBSS. After the addition of 20 µl of charging buffer (Membrane Potential Assay Kit Explorer $R^{8126}$, Molecular Devices GmbH, Ismaning) and 20 µl of the substance to be tested in a suitable concentration, incubation is continued for a further 30 min. at 37° C., 5% $CO_2$. The measurement is carried out in the Fluorescent Imaging Plate Reader (Molecular Devices GmbH, Ismaning) at an excitation wavelength of 485 nm and is started by the addition of 20 µl of stimulant buffer (140 mM NaCl and 120 mM glucose). The depolarisation of the cell caused by the glucose-induced influx of $Na^+$ can be measured and quantified as a change in fluorescence.

The compounds of general formula I according to the invention may for example have EC50 values of less than 1000 nM, particularly less than 200 nM, particularly preferably less than 50 nM.

In view of their ability to inhibit the SGLT activity, the compounds of general formula I according to the invention and the corresponding pharmaceutically acceptable salts thereof are theoretically suitable for the treatment and/or preventative treatment of all those conditions or diseases which may be affected by the inhibition of the SGLT activity, particularly the SGLT-2 activity. Therefore, compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia. These substances are also suitable for preventing beta-cell degeneration such as e.g. apoptosis or necrosis of pancreatic beta cells. The substances are also suitable for improving or restoring the functionality of pancreatic cells, and also for increasing the number and size of pancreatic beta cells. The compounds according to the invention may also be used as diuretics or antihypertensives and are suitable for the prevention and treatment of acute renal failure.

In particular, the compounds according to the invention, including the physiologically acceptable salts thereof, are suitable for the prevention or treatment of diabetes, particularly type 1 and type 2 diabetes mellitus, and/or diabetic complications.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, solutions, suspensions or suppositories.

The compounds according to the invention may also be used in conjunction with other active substances, particularly for the treatment and/or prevention of the diseases and conditions mentioned above. Other active substances which are suitable for such combinations include, in particular, those which potentiate the therapeutic effect of an SGLT inhibitor according to the invention with respect to one of the indications mentioned and/or which allow the dosage of an SGLT inhibitor according to the invention to be reduced. Therapeutic agents which are suitable for such a combination include, for example, antidiabetic agents such as metformin, sulphonylureas (e.g. glibenclamide, tolbutamide, glimepiride), nateglinide, repaglinide, thiazolidinediones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. LAF237, MK-431), alpha2-antagonists, insulin and insulin analogues, GLP-1 and GLP-1 analogues (e.g. exendin-4) or amylin. Other active substances which are suitable as combination partners include inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-increasing compounds such as CETP inhibitors or ABC1 regulators or active substances for treating obesity, such as sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully 1/5 of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the sodium-dependent glucose cotransporter SGLT. These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

In the foregoing and following text, H atoms of hydroxyl groups are not explicitly shown in every case in structural formulae. The Examples that follow are intended to illustrate the present invention without restricting it:

Preparation of the Starting Compounds:

EXAMPLE I

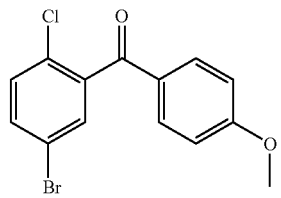

(5-bromo-2-chloro-phenyl)-(4-methoxy-phenyl)-methanone 38.3 ml oxalyl chloride and 0.8 ml of dimethylformamide are added to a mixture of 100 g 5-bromo-2-chloro-benzoic acid in 500 ml dichloromethane. The reaction mixture is stirred for 14 h, then filtered and separated from all volatile constituents in the rotary evaporator getrennt. The residue is dissolved in 150 ml dichloromethane, the solution is cooled to −5° C., and 46.5 g anisole are added. Then 51.5 g aluminium trichloride are added batchwise such that the temperature does not exceed 5° C. The solution is stirred for another 1 h at 1-5° C. and then poured onto ice. The organic phase is separated off and the aqueous phase is extracted another three times with dichloromethane. The combined organic phases are washed with aqueous 1 M hydrochloric acid, twice with 1 M sodium hydroxide solution and with saturated sodium chloride solution. Then the organic phase is dried, the solvent is removed and the residue is recrystallised from ethanol.

Yield: 86.3 g (64% of theory)

Mass spectrum (ESI$^+$): m/z=325/327/329 (bromine+chlorine) [M+H]$^+$

EXAMPLE II

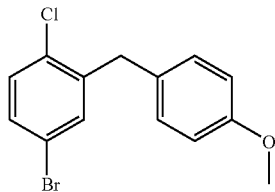

4-bromo-1-chloro-2-(4-methoxy-benzyl)-benzene

A solution of 86.2 g (5-bromo-2-chloro-phenyl)-(4-methoxy-phenyl)-methanone and 101.5 ml triethylsilane in 75 ml dichloromethane and 150 ml acetonitrile is cooled to 10° C. Then 50.8 ml boron trifluoride etherate are added with stirring such that the temperature does not exceed 20° C. The solution is stirred for 14 h at ambient temperature, before another 9 ml triethylsilane and 4.4 ml boron trifluoride etherate are added. The solution is stirred for a further 3 h at 45-50° C. and then cooled to ambient temperature. A solution of 28 g potassium hydroxide in 70 ml of water is added and the mixture is stirred for 2 h. Then the organic phase is separated off and the aqueous phase is extracted another three times with diisopropylether. The combined organic phases are washed twice with 2 M potassium hydroxide solution and once with aqueous sodium chloride solution and then dried over sodium sulphate. After the solvent has been eliminated the residue is stirred into ethanol, separated off again and dried at 60° C.

Yield: 50.0 g (61% of theory)

Mass spectrum (ESI$^+$): m/z=310/312/314 (bromine+chlorine) [M+H]$^+$

EXAMPLE III

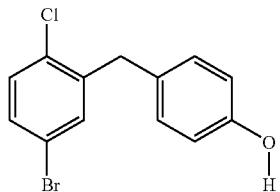

4-(5-bromo-2-chloro-benzyl)-phenol

A solution of 14.8 g 4-bromo-1-chloro-2-(4-methoxy-benzyl)-benzene in 150 ml dichloromethane is cooled in the ice bath. Then 50 ml of a 1 M solution of boron tribromide in dichloromethane are added and the solution is stirred for 2 h at ambient temperature. The solution is then cooled again in the ice bath, and saturated potassium carbonate solution is added dropwise. At ambient temperature the mixture is adjusted to a pH of 1 with aqueous 1 M hydrochloric acid, the organic phase is separated off and the aqueous phase is extracted another three times with ethyl acetate. The combined organic phases are dried over sodium sulphate, and the solvent is totally eliminated.

Yield: 13.9 g (98% of theory)

Mass spectrum (ESI$^-$): m/z=295/297/299 (Br+Cl) [M−H]$^-$

EXAMPLE IV

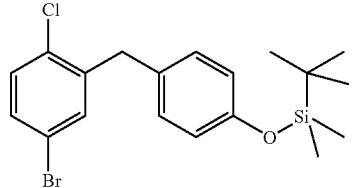

[4-(5-bromo-2-chloro-benzyl)-phenoxy]-tert-butyl-dimethyl-silane

A solution of 13.9 g 4-(5-bromo-2-chloro-benzyl)-phenol in 140 ml dichloromethane is cooled in the ice bath. Then 7.54 g tert-butyldimethylsilyl chloride in 20 ml dichloromethane are added, followed by 9.8 ml triethylamine and 0.5 g dimethylaminopyridine. The solution is stirred for 16 h at ambient temperature and then diluted with 100 ml dichloromethane. The organic phase is washed twice with aqueous 1 M hydrochloric acid and once with aqueous sodium hydrogen carbonate solution and then dried over sodium sulphate. After the solvent has been eliminated the residue is filtered on silica gel (cyclohexane/ethyl acetate 100:1).

Yield: 16.8 g (87% of theory)

Mass spectrum (EI): m/z=410/412/414 (Br+Cl) [M]$^+$

EXAMPLE V

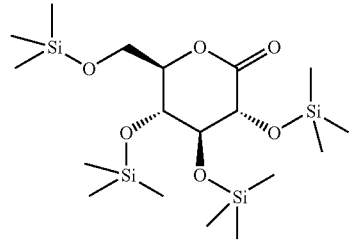

2,3,4,6-tetrakis-O-(trimethylsilyi)-D-glucopyranone

A solution of 20 g D-glucono-1,5-lactone and 98.5 ml N-methylmorpholine in 200 ml of tetrahydrofuran is cooled to −5° C. Then 85 ml trimethylsilyl chloride are added dropwise such that the temperature does not exceed 5° C. The solution is then stirred for 1 h at ambient temperature, 5 h at 35° C. and another 14 h at ambient temperature. After the addition of 300 ml of toluene the solution is cooled in the ice bath, and 500 ml of water are added such that the temperature does not exceed 10° C. The organic phase is then separated off and washed once each with aqueous sodium dihydrogen phosphate solution, water and saturated aqueous sodium chloride solution. The solvent is removed, the residue is taken up in 250 ml of toluene and the solvent is again eliminated completely.

Yield: 52.5 g (approx. 90% pure)

Mass spectrum (ESI⁺): m/z=467 [M+H]⁺

EXAMPLE VI

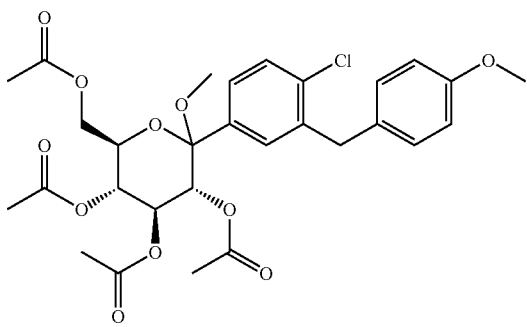

1-chloro-4-(2,3,4,6-tetra-O-acetyl-1-methoxy-D-glucopyranos-1-yl)-2-(4-methoxybenzyl)-benzene A solution of 1.0 g 4-bromo-1-chloro-2-(4-methoxy-benzyl)-benzene in 14 ml dry diethyl ether is cooled to −80° C. under argon. 4.0 ml of a 1.7 M solution of tert-butyllithium in pentane are slowly added dropwise to the cooled solution, and then the solution is stirred for 30 min at −80° C. This solution is then added dropwise through a transfer needle cooled with dry ice to a solution of 1.61 g of 2,3,4,6-tetrakis-O-(trimethylsilyl)-D-glucopyranone in 10 ml diethyl ether, cooled to −80° C. The resulting solution is stirred for 4 h at −78° C. Then a solution of 0.4 ml methanesulphonic acid in 12 ml of methanol is added and the solution is stirred for 16 h at ambient temperature. The solution is then neutralised with ethyldiisopropylamine and evaporated down. The residue is taken up in toluene and evaporated down again. Then the residue is dissolved in 8 ml of toluene and 3.4 ml ethyldiisopropylamine are added to the solution. The solution is cooled in the ice bath and then 1.4 ml acetic anhydride and 0.04 g dimethylaminopyridine are added. The solution is stirred for 6 h at ambient temperature and then combined with aqueous sodium hydrogen carbonate solution. The organic phase is separated off and the aqueous phase is extracted with ethyl acetate. After the combined organic extracts have been dried over sodium sulphate and the solvent has been eliminated the residue is chromatographed on silica gel (cyclohexane/ethyl acetate 6:1->1:1).

Yield: 1.55 g (85% of theory)

Mass spectrum (ESI⁺): m/z=610/612 (chlorine) [M+NH₄]⁺

EXAMPLE VII

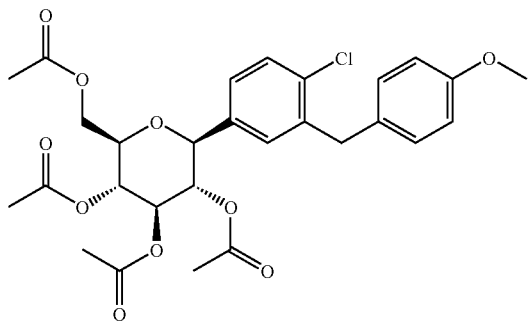

1-chloro-4-(2,3,4,6-tetra-O-acetyl-β-D-glucopyranos-1-yl)-2-(4-methoxy-benzyl)-benzene A solution of 1.44 g 1-chloro-4-(2,3,4,6-tetra-O-acetyl-1-methoxy-D-glucopyranos-1-yl)-2-(4-methoxybenzyl)-benzene in 20 ml acetonitrile and 44 µl water is cooled in the ice bath. Then 1.2 ml triethylsilane and 0.26 ml boron trifluoride etherate are added. The solution is stirred for 1 h in the ice bath and then at ambient temperature. After 3 and 5 h a further 0.72 ml triethylsilane and 0.15 ml boron trifluoride etherate are added in each case. After another 12 h stirring at ambient temperature aqueous sodium hydrogen carbonate solution is added, the mixture is stirred for 0.5 h and then extracted with ethyl acetate. The organic phase is dried over sodium sulphate, concentrated and chromatographed on silica gel (cyclohexane/ethyl acetate 8:1->1:1).

Yield: 1.12 g (82% of theory)

Mass spectrum (ESI⁺): m/z=580/582 (chlorine) [M+NH₄]⁺

EXAMPLE VIII

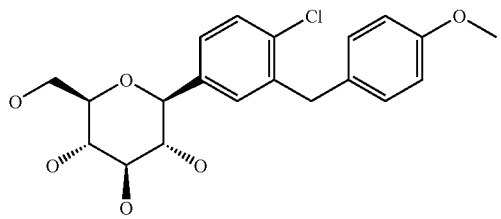

1-chloro-2-(4-methoxy-benzyl)-4-(β-D-glucopyranos-1-yl)-benzene 2 ml 4 M potassium hydroxide solution are added to a solution of 1.00 g 1-chloro-4-(2,3,4,6-tetra-O-acetyl-β-D-glucopyranos-1-yl)-2-(4-methoxy-benzyl)-benzene in 20 ml of methanol. The solution is stirred for 8 h at ambient temperature and then neutralised with 1 M hydrochloric acid. The solution is freed from methanol, combined with aqueous sodium chloride solution and extracted with ethyl acetate. The organic phase is dried over sodium sulphate and the solvent is removed. The residue is purified on silica gel (dichloromethane/methanol 1:0->3:1).

Yield: 0.64 g (91% of theory)

Mass spectrum (ESI⁺): m/z=412/414 (chlorine) [M+NH₄]⁺

EXAMPLE IX

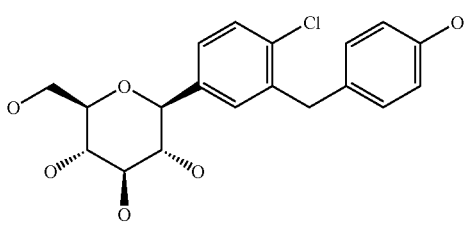

1-chloro-4-(β-D-glucopyranos-1-yl)-2-(4-hydroxy-benzyl)-benzene

A solution of 4.0 g [4-(5-bromo-2-chloro-benzyl)-phenoxy]-tert-butyl-dimethyl-silane in 42 ml dry diethyl ether is cooled to −80° C. under argon. 11.6 ml of a 1.7 M solution of tert-butyllithium in pentane are slowly added dropwise to the cooled solution, and then the solution is stirred for 30 min at −80° C. This solution is then added dropwise through a transfer needle cooled with dry ice to a solution of 4.78 g of 2,3,4,6-tetrakis-O-(trimethylsilyl)-D-glucopyranone in 38 ml diethyl ether, cooled to −80° C. Then a solution of 1.1 ml methanesulphonic acid in 35 ml of methanol is added and the solution is stirred for 16 h at ambient temperature. The solution is then neutralised with solid sodium hydrogen carbonate, ethyl acetate is added and the methanol is removed together with the ether. Aqueous sodium hydrogen carbonate solution is added to the remaining solution and the mixture is extracted four times with ethyl acetate. The organic phases are dried over sodium sulphate and evaporated down. The residue is dissolved in 30 ml acetonitrile and 30 ml dichloromethane and the solution is cooled to −10° C. After the addition of 4.4 ml triethylsilane 2.6 ml boron trifluoride etherate are added dropwise such that the temperature does not exceed −5° C. After all the solution has been added the resulting solution is stirred for another 5 h at −5 to −10° C. and then quenched by the addition of aqueous sodium hydrogen carbonate solution. The organic phase is separated off and the aqueous phase is extracted four times with ethyl acetate. The combined organic phase are dried over sodium sulphate, the solvent is removed and the residue is purified on silica gel. The product thus obtained is a roughly 6:1 mixture of β/α, which can be converted into the pure β-anomer by total acetylation of the hydroxy groups with acetic anhydride and pyridine in dichloromethane and recrystallisation of the product from ethanol. The product thus obtained is converted into the title compound by reaction with 4 M potassium hydroxide solution in methanol.

Yield: 1.6 g (46% of theory)

Mass spectrum (ESI$^+$): m/z=398/400 (Cl) [M+H]$^+$

EXAMPLE X

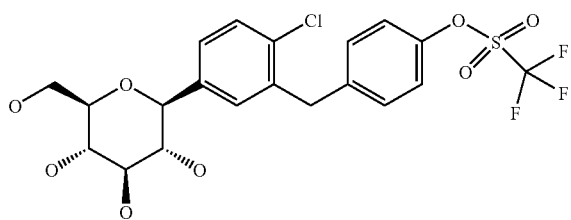

1-chloro-4-(β-D-glucopyranos-1-yl)-2-[4-(trifluoromethylsulphonyloxy)-benzyl]-benzene 10 mg 4-dimethylaminopyridine are added to a solution of 0.38 g 1-chloro-4-(β-D-glucopyranos-1-yl)-2-(4-hydroxybenzyl)-benzene, 0.21 ml triethylamine and 0.39 g N,N-bis-(trifluoromethanesulphonyl)-aniline in 10 ml dry dichloromethane. The solution is stirred for 4 h at ambient temperature and then combined with aqueous sodium chloride solution. It is extracted with ethyl acetate, the organic extracts are dried over sodium sulphate, and the solvent is removed. The residue is chromatographed on silica gel (dichloromethane/methanol 1:0->4:1).

Yield: 0.33 g (64% of theory)

Mass spectrum (ESI$^+$): m/z=530/532 (Cl) [M+NH$_4$]$^+$

EXAMPLE XI

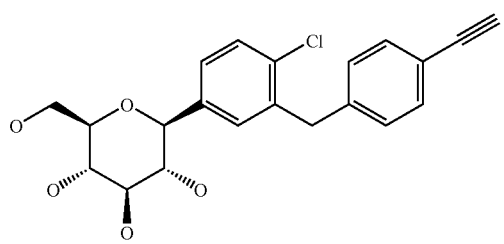

1-chloro-4-(β-D-glucopyranos-1-yl)-2-(4-ethynyl-benzyl)-benzene

Under argon, 25 mg copper iodide, 44 mg bis-(triphenylphosphine)-palladium dichloride, 0.30 ml triethylamine and finally 0.14 ml trimethylsilylacetylene are added to a solution of 0.32 g 1-chloro-4-(β-D-glucopyranos-1-yl)-2-[4-(trifluoromethylsulphonyloxy)-benzyl]-benzene in 3 ml of dimethylformamide. The flask is tightly sealed and the mixture is stirred for 8 h at 90° C. Then another 25 mg bis-(triphenylphosphine)-palladium dichloride and 0.1 ml trimethylsilylacetylene are added, and the solution is stirred for a further 10 h at 90° C. Then aqueous sodium hydrogen carbonate solution is added, the mixture is extracted three times with ethyl acetate, and the collected organic phases are dried over sodium sulphate. After the solvent has been eliminated the residue is dissolved in 5 ml of methanol and combined with 0.12 g potassium carbonate. The mixture is stirred for 1 h at ambient temperature and then neutralised with 1 M hydrochloric acid. Then the methanol is evaporated off, the residue is combined with aqueous sodium chloride solution and extracted with ethyl acetate. The organic extracts collected are dried over sodium sulphate, and the solvent is removed. The residue is chromatographed on silica gel (dichloromethane/methanol 1:0->5:1).

Yield: 0.095 g (40% of theory)

Mass spectrum (ESI$^+$): m/z=406/408 (Cl) [M+NH$_4$]$^+$

EXAMPLE XII

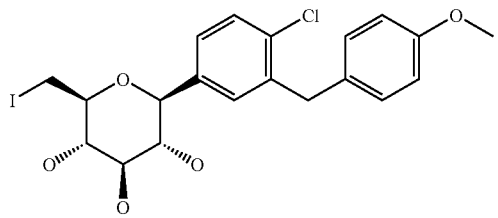

1-chloro-2-(4-methoxy-benzyl)-4-(6-desoxy-6-iodo-β-D-glucopyranos-1-yl)-benzene 0.53 g triphenylphosphine, 0.13 g imidazole and 0.48 g iodine are added to a solution of 0.60 g 1-chloro-2-(4-methoxy-benzyl)-4-(β-D-glucopyranos-1-yl)-benzene in 5 ml dichloromethane. The solution is stirred for 18 h at 40-45° C. and then diluted with 30 ml dichloromethane. The solution is washed with 1 M hydrochloric acid, dried over sodium sulphate and freed from the solvent. The residue is purified on silica gel (dichloromethane/methane 1:0->20:1).

Yield: 0.66 g (87% of theory)
Mass spectrum (ESI$^+$): m/z=522/524 (chlorine) [M+NH$_4$]$^+$

EXAMPLE XIII

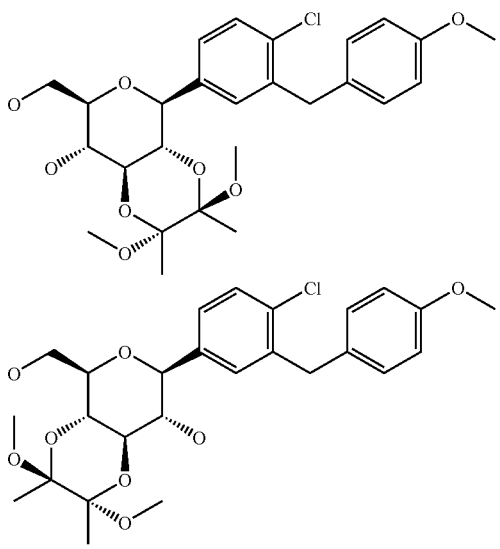

1-chloro-2-(4-methoxy-benzyl)-4-[2,3-O-(2,3-dimethoxy-but-2,3-diyl)-β-D-glucopyranos-1-yl]-benzene and 1-chloro-2-(4-methoxy-benzyl)-4-[3,4-O-(2,3-dimethoxy-but-2,3-diyl)-β-D-glucopyranos-1-yl]-benzene 0.49 ml diacetyl, 1.2 ml methyl orthoformate and 0.64 ml boron trifluoride etherate are added successively to a solution of 1.0 g 1-chloro-2-(4-methoxy-benzyl)-4-(β-D-glucopyranos-1-yl)-benzene in 14 ml of methanol heated to 60° C. The solution is stirred for 4 h at 60° C. and then cooled to ambient temperature. At ambient temperature 3 ml triethylamine are added and the solution is stirred for 0.5 h. Then the solution is evaporated down and the residue is purified on silica gel (cyclohexane/ethyl acetate 4:1->1:1).

Yield: 1-chloro-2-(4-methoxy-benzyl)-4-[2,3-O-(2,3-dimethoxy-but-2,3-diyl)-β-D-glucopyranos-1-yl]-benzene: 0.70 g (54% of theory)
Mass spectrum (ESI$^+$): m/z=526/528 (chlorine) [M+NH$_4$]$^+$
1-chloro-2-(4-methoxy-benzyl)-4-[3,4-O-(2,3-dimethoxy-but-2,3-diyl)-β-D-glucopyranos-1-yl]-benzene: 0.54 g (42% of theory)
Mass spectrum (ESI$^+$): m/z=526/528 (chlorine) [M+NH$_4$]$^+$

EXAMPLE XIV

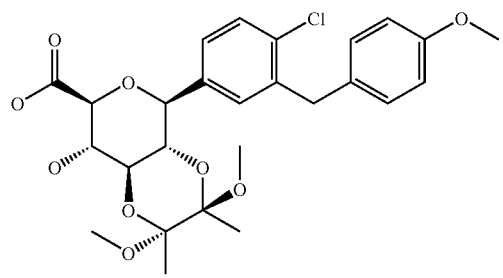

5-[4-chloro-3-(4-methoxy-benzyl)-phenyl]-8-hydroxy-2,3-dimethoxy-2,3-dimethylhexahydro-pyran[3,4-b][1,4]dioxin-7-carboxylic acid 8 mg 2,2,6,6-Tetramethylpiperidin-1-yloxy followed by a solution of 0.32 g potassium bromide and 0.42 g tetrabutylammonium bromide in 57 ml saturated sodium hydrogen carbonate solution are added to an ice-cold solution of 1.40 g 1-chloro-2-(4-methoxy-benzyl)-4-[2,3-O-(2,3-dimethoxy-but-2,3-diyl)-β-D-glucopyranos-1-yl]-benzene in 28 ml dichloromethane. A solution of 5.7 ml saturated aqueous sodium chloride solution, 2.8 ml saturated aqueous sodium hydrogen carbonate solution and 7.7 ml sodium hypochlorite solution (12% active chlorine) is added dropwise with vigorous stirring. After 1 and 2 h stirring, a solution of 1.2 ml saturated aqueous sodium chloride solution, 0.6 ml saturated aqueous sodium hydrogen carbonate solution and 1.6 ml sodium hypochlorite solution (12% active chlorine) are each added dropwise. After another hour in the ice bath the solution is adjusted to pH=1 with 4 M hydrochloric acid and extracted with dichloromethane (1×) and ethyl acetate (3×). After drying over sodium sulphate the solvent is removed and the residue is purified on silica gel (dichloromethane/methanol 1:0->10:1).

Yield: 0.92 g (64% of theory)
Mass spectrum (ESI$^+$): m/z=540/542 (chlorine) [M+NH$_4$]$^+$ The following compound is obtained analogously to Example XIV:

(1) 7-[4-chloro-3-(4-methoxy-benzyl)-phenyl]-8-hydroxy-2,3-dimethoxy-2,3-dimethyl-hexahydro-pyran[3,4-b][1,4]dioxin-5-carboxylic acid

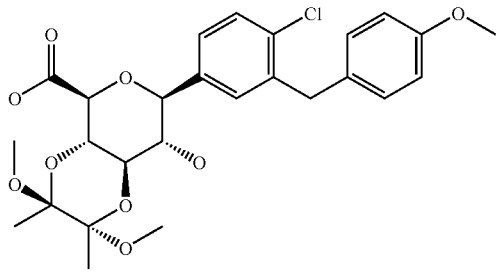

Mass spectrum (ESI$^+$): m/z=540/542 (chlorine) [M+NH$_4$]$^+$

Preparation of the Final Compounds:

EXAMPLE 1

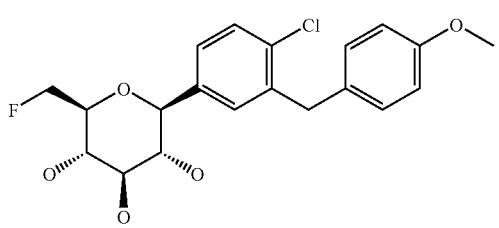

1-chloro-2-(4-methoxy-benzyl)-4-(6-desoxy-6-fluoro-β-D-glucopyranos-1-yl)-benzene 0.20 ml diethylaminosulphur trifluoride in 0.5 ml dichloromethane are added dropwise to a solution of 0.10 g 1-chloro-2-(4-methoxy-benzyl)-4-(β-D-glucopyranos-1-yl)-benzene in 2.5 ml dichloromethane, cooled to −40° C. The solution is allowed to warm up to ambient temperature in the cooling bath and then stirred for 2 h at ambient temperature. Then the solution is cooled to −40° C. and combined with 2 ml of methanol. After heating to ambient temperature the solution is evaporated down and the residue is chromatographed on silica gel (dichloromethane/methanol 1:0->8:1).

Yield: 0.038 g (38% of theory)

Mass spectrum (ESI$^+$): m/z=414/416 (chlorine) [M+NH$_4$]$^+$

The following compound is obtained analogously to Example 1:

(1) 1-chloro-2-(4-ethynyl-benzyl)-4-(6-desoxy-6-fluoro-β-D-glucopyranos-1-yl)-benzene

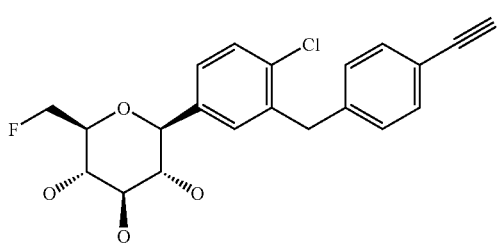

EXAMPLE 2

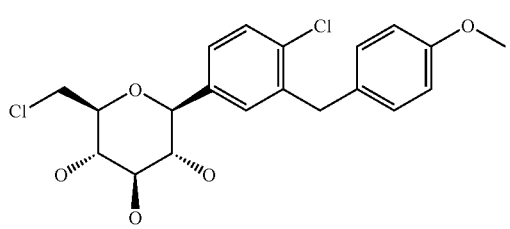

1-chloro-2-(4-methoxy-benzyl)-4-(6-desoxy-6-chloro-β-D-glucopyranos-1-yl)-benzene 50 μl carbon tetrachloride are added to a solution of 0.15 g 1-chloro-2-(4-methoxybenzyl)-4-(β-D-glucopyranos-1-yl)-benzene and 0.11 g triphenylphosphine in 2 ml dichloromethane. The solution is stirred for 24 h at 45° C., before another 0.11 g triphenylphosphine and 100 μl carbon tetrachloride are added. After a further 12 h stirring at 45° C. the solvent is removed and the residue is purified on silica gel (dichloromethane/methanol 1:0->15:1).

Yield: 0.11 g (70% of theory)

Mass spectrum (ESI$^+$): m/z=430/432/434 (2 chlorine) [M+NH$_4$]$^+$

EXAMPLE 3

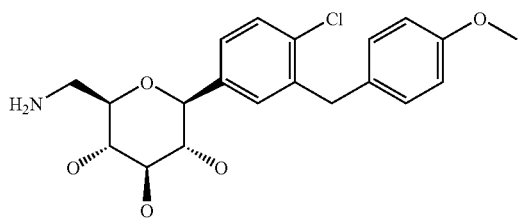

1-chloro-2-(4-methoxy-benzyl)-4-(6-desoxy-6-amino-β-D-qlucopyranos-1-yl)-benzene 0.19 g triphenylphosphine, 0.09 g phthalimide and finally 0.14 ml diisopropyl azodicarboxylate are added to a solution of 0.20 g 1-chloro-2-(4-methoxy-benzyl)-4-(β-D-glucopyranos-1-yl)-benzene in 3.5 ml of tetrahydrofuran. The solution is stirred for 2 h at ambient temperature and then diluted with methanol and evaporated down. The residue is purified on silica gel (dichloromethane/methanol 1:0->8:1). The purified phthalic acid-protected intermediate product is dissolved in 2 ml of ethanol and 2 ml of toluene and combined with 0.25 g ethanolamine. The solution is stirred for 5 h at 80° C. and then combined with aqueous potassium carbonate solution. The solution is extracted with ethyl acetate, the organic extracts are dried over sodium sulphate, and then the solvent is distilled off. The residue is chromatographed on silica gel (dichloromethane/methanol 1:0->1:1).

Yield: 0.086 g (43% of theory)

Mass spectrum (ESI$^+$): m/z=394/396 (chlorine) [M+H]$^+$

EXAMPLE 4

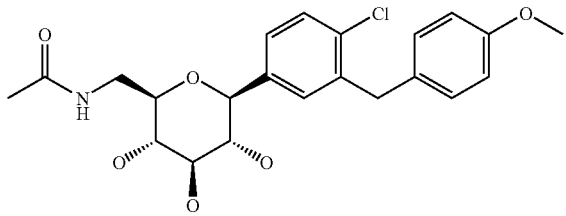

1-chloro-2-(4-methoxy-benzyl)-4-(6-desoxy-6-acetylamino-β-D-glucopyranos-1-yl)-benzene 0.1 ml acetic anhydride and 10 mg 4-dimethylaminopyridine are added to an ice-cooled solution of 0.078 g 1-chloro-2-(4-methoxy-benzyl)-4-(6-desoxy-6-amino-β-D-glucopyranos-1-yl)-benzene and 0.1 ml of pyridine in 2 ml dichloromethane. The solution is stirred for 1 h at ambient temperature and then diluted with 20 ml dichloromethane. The diluted solution is washed with 1 M hydrochloric acid, and the solvent is eliminated. The residue is dissolved in 4 ml of methanol and the solution is cooled in the ice bath. After the addition of 1 ml of 4 M potassium hydroxide solution the mixture is stirred for 1 h at ambient temperature. The solution is then neutralized with 1 M hydrochloric acid and the methanol is distilled off. Aqueous sodium hydrogen carbonate solution is added, the solution is extracted with ethyl acetate, and the organic extracts are dried over sodium sulphate. After the solvent has been eliminated the residue is chromatographed on silica gel (dichloromethane/methanol 1:0->8:1).

Yield: 0.078 g (90% of theory)
Mass spectrum (ESI$^+$): m/z=436/438 (chlorine) [M+H]$^+$

EXAMPLE 5

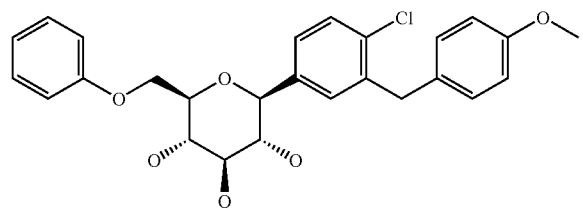

1-chloro-2-(4-methoxy-benzyl)-4-(6-O-phenyl-1-D-glucopyranos-1-yl)-benzene 0.19 g triphenylphosphine, 56 mg phenol and finally 0.14 ml diisopropyl azodicarboxylate are added to a solution of 0.20 g 1-chloro-2-(4-methoxy-benzyl)-4-(β-D-glucopyranos-1-yl)-benzene in 3.5 ml of tetrahydrofuran. The solution is stirred at ambient temperature. After 1 h a further 0.18 g triphenylphosphine and 0.14 ml diisopropyl azodicarboxylate are added and after 2 and 4 h 50 mg phenol are added in each case. After a total of 18 h stirring at ambient temperature methanol is added and the solution is evaporated down completely. The residue is purified on silica gel Yield: 0.13 g (55% of theory)
Mass spectrum (ESI$^+$): m/z=488/490 (chlorine) [M+NH$_4$]$^+$ The following compounds are obtained analogously to Example 5:

(1) 1-chloro-2-(4-methoxy-benzyl)-4-(6-cyano-6-desoxy-β-D-glucopyranos-1-yl)-benzene

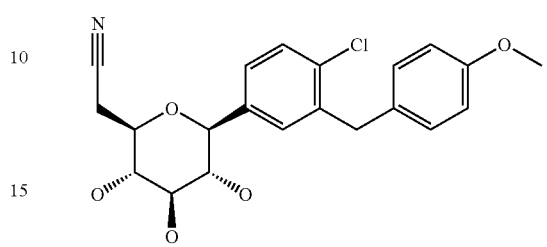

The reaction is carried out with 2-cyano-2-hydroxy-propane instead of phenol and at 45-50° C.
Mass spectrum (ESI$^+$): m/z=421/423 (chlorine) [M+NH$_4$]$^+$ (2) 1-chloro-2-(4-ethynyl-benzyl)-4-(6-cyano-6-desoxy-β-D-glucopyranos-1-yl)-benzene

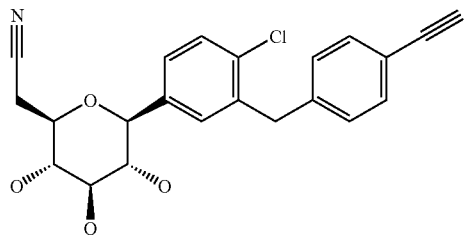

The reaction is carried out with 2-cyano-2-hydroxy-propane instead of phenol and at 45-50° C.

EXAMPLE 6

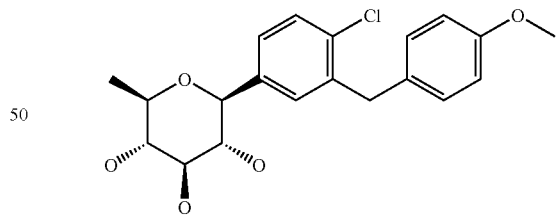

1-chloro-2-(4-methoxy-benzyl)-4-(6-desoxy-β-D-glucopyranos-1-yl)-benzene 0.95 ml tris-(trimethylsilyl)silane and 12 mg azobisisobutyronitrile are added to a solution of 0.10 g 1-chloro-2-(4-methoxy-benzyl)-4-(6-desoxy-6-iodo-β-D-glucopyranos-1-yl)-benzene in 1.5 ml of toluene. The solution is stirred for 22 h at 120° C. in the tightly sealed flask and then diluted with methanol. The solution is evaporated down, the residue is combined with 1 M hydrochloric acid and extracted with ethyl acetate. The organic extracts are dried over sodium sulphate, and the solvent is then removed. The residue is purified on silica gel (dichloromethane/methanol 1:0->10:1).

Yield: 0.062 g (83% of theory)

Mass spectrum (ESI$^+$): m/z=396/398 (chlorine) [M+NH$_4$]$^+$

EXAMPLE 7

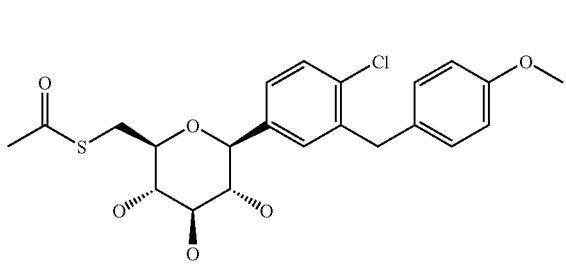

1-chloro-2-(4-methoxy-benzyl)-4-(6-desoxy-6-acetylsulphanyl-β-D-qlucopyranos-1-yl)-benzene 0.58 g caesium carbonate are added to an ice-cooled solution of 0.23 g 1-chloro-2-(4-methoxy-benzyl)-4-(6-desoxy-6-iodo-β-D-glucopyranos-1-yl)-benzene and 0.15 ml thioacetic acid in 3 ml of dimethylformamide. The mixture is stirred for 14 h at ambient temperature and then combined with aqueous sodium hydrogen carbonate solution. It is then extracted with ethyl acetate, the organic phase is dried over sodium sulphate and the solvent is eliminated. The residue is chromatographed on silica gel (dichloromethane/methanol 1:0->10:1).

Yield: 0.185 g (90% of theory)

Mass spectrum (ESI$^+$): m/z=470/472 (chlorine) [M+NH$_4$]$^+$

EXAMPLE 8

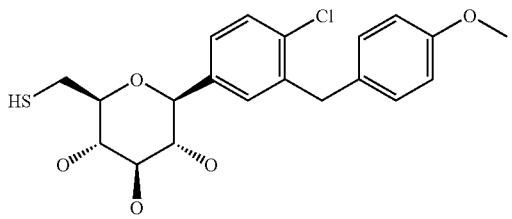

1-chloro-2-(4-methoxy-benzyl)-4-(6-desoxy-6-mercapto-β-D-glucopyranos-1-yl)-benzene 0.12 ml of a 4 M potassium hydroxide solution are added to an ice-cooled solution of 0.145 g 1-chloro-2-(4-methoxy-benzyl)-4-(6-desoxy-6-acetylsulphanyl-β-D-glucopyranos-1-yl)-benzene in 2.5 ml of methanol. The solution is stirred for 1 h at ambient temperature and then neutralised with 1 M hydrochloric acid. After elimination of the methanol aqueous sodium chloride solution is added, the mixture is extracted with ethyl acetate and the organic phase is dried over sodium sulphate. The organic phase is evaporated down and the residue is purified on silica gel (dichloromethane/methanol 1:0->10:1).

Yield: 0.105 g (80% of theory)

Mass spectrum (ESI$^+$): m/z=428/430 (chlorine) [M+NH$_4$]$^+$

EXAMPLE 9

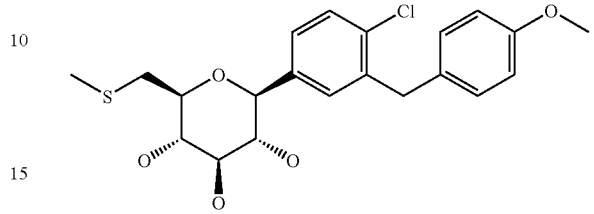

1-chloro-2-(4-methoxy-benzyl)-4-(6-desoxy-6-methylsulphanyl-β-D-glucopyranos-1-yl)-benzene 0.095 g caesium carbonate are added to an ice-cooled solution of 0.082 g 1-chloro-2-(4-methoxy-benzyl)-4-(6-desoxy-6-mercapto-β-D-glucopyranos-1-yl)-benzene in 2 ml of dimethylformamide. The solution is stirred for 5 min in the ice bath and then combined with 16 μl methyl iodide. The solution is stirred for 1 h at ambient temperature and then diluted with water. The aqueous phase is extracted with ethyl acetate, the organic phase is dried over sodium sulphate and the solvent is eliminated. The residue is purified on silica gel (dichloromethane/methanol 1:0->10:1).

Yield: 0.014 g (17% of theory)

Mass spectrum (ESI$^+$): m/z=442/444 (chlorine) [M+NH$_4$]$^+$

EXAMPLE 10

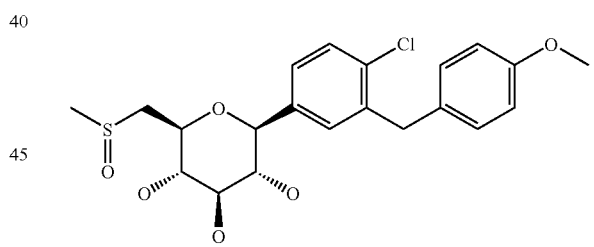

1-chloro-2-(4-methoxy-benzyl)-4-(6-desoxy-6-methylsulphinyl-β-D-glucopyranos-1-yl)-benzene 0.1 ml hydrogen peroxide solution (35% in water) is added to an ice-cooled solution of 0.16 g 1-chloro-2-(4-methoxy-benzyl)-4-(6-desoxy-6-methylsulphanyl-β-D-glucopyranos-1-yl)-benzene in 7 ml 1,1,1,3,3,3-hexafluorisopropanol. The solution is stirred for 1 h in the ice bath and then for 2 h at ambient temperature. Then aqueous sodium thiosulphate solution and sodium hydrogen carbonate solution are added and the mixture is extracted with ethyl acetate. The organic extracts are dried over sodium sulphate, and the solvent is removed. The residue is purified on silica gel (dichloromethane/methanol 1:0->5:1).

Yield: 0.12 g (72% of theory)

Mass spectrum (ESI$^+$): m/z=441/443 (chlorine) [M+H]$^+$

EXAMPLE 11

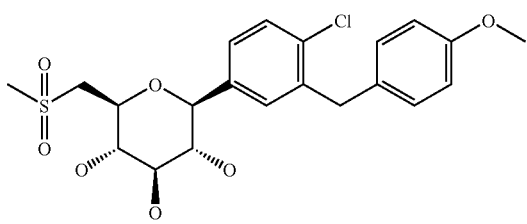

1-chloro-2-(4-methoxy-benzyl)-4-(6-desoxy-6-methylsulphonyl-β-D-glucopyranos-1-yl)-benzene 0.31 g meta-chloroperbenzoic acid (77% in water) are added to an ice-cooled solution of 0.26 g 1-chloro-2-(4-methoxy-benzyl)-4-(6-desoxy-6-methylsulphanyl-β-D-glucopyranos-1-yl)-benzene in 8 ml dichloromethane. The solution is stirred for 1 h in the ice bath and then for 2 h at ambient temperature. Then aqueous sodium thiosulphate solution and sodium hydrogen carbonate solution are added and the mixture is extracted with ethyl acetate. The organic extracts are dried over sodium sulphate, and the solvent is removed. The residue is purified on silica gel (dichloromethane/methanol 1:0->10:1).

Yield: 0.19 g (68% of theory)
Mass spectrum (ESI$^+$): m/z=474/476 (chlorine) [M+NH$_4$]$^+$

EXAMPLE 12

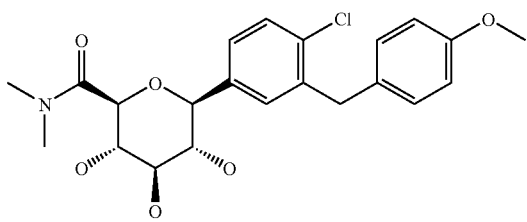

6-[4-chloro-3-(4-methoxy-benzyl)-phenyl]-3,4,5-trihydroxy-tetrahydro-pyran-2-carboxylic acid dimethylamide 0.13 g O-(benzotriazol-1-yl)-N,N, N',N'-tetramethyluronium tetrafluoroborate are added to an ice-cooled solution of 0.15 g 5-[4-chloro-3-(4-methoxy-benzyl)-phenyl]-8-hydroxy-2,3-dimethoxy-2,3-dimethyl-hexahydro-pyran[3,4-b][1,4]dioxin-7-carboxylic acid in 2 ml of dimethylformamide. After 15 min stirring in the ice bath 0.2 ml of a solution of dimethylamine in tetrahydrofuran (2 M) and 0.09 ml diisopropylethylamine are added. After 2 h stirring in the ice bath aqueous potassium carbonate solution is added and the mixture is extracted with ethyl acetate. After drying on sodium sulphate the solvent is removed and the residue is taken up in 2.5 ml trifluoroacetic acid (80% in water). The solution is stirred for 2 h at ambient temperature and then neutralised with 4 M potassium hydroxide solution. The solution is extracted with ethyl acetate, the organic phase is dried over sodium sulphate and the solvent is eliminated. The residue is purified on silica gel (dichloromethane/methanol 1:0->15:1).

Yield: 0.11 g (86% of theory)
Mass spectrum (ESI$^+$): m/z=436/438 (chlorine) [M+H]$^+$ The following compounds are obtained analogously to Example 12:

(1) 6-[4-chloro-3-(4-methoxy-benzyl)-phenyl]-3,4,5-trihydroxy-tetrahydro-pyran-2-carboxylic acid amide

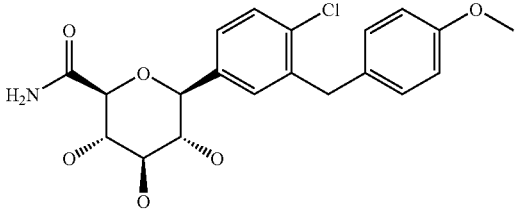

Mass spectrum (ESI$^+$): m/z=408/410 (chlorine) [M+H]$^+$ (2) 6-[4-chloro-3-(4-methoxy-benzyl)-phenyl]-3,4,5-trihydroxy-tetrahydro-pyran-2-carboxylic acid methylamide

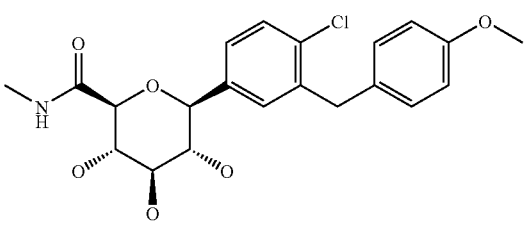

Mass spectrum (ESI$^+$): m/z=422/424 (chlorine) [M+H]$^+$ (3) 6-[4-chloro-3-(4-methoxy-benzyl)-phenyl]-3,4,5-trihydroxy-tetrahydro-pyran-2-carboxylic acid benzylamide

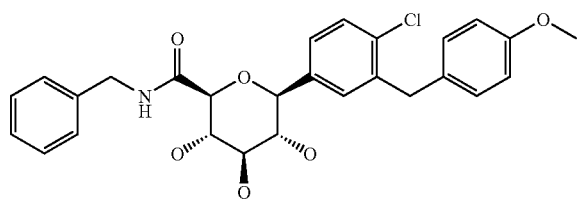

Mass spectrum (ESI$^+$): m/z=408/410 (chlorine) [M+H]$^+$

EXAMPLE 13

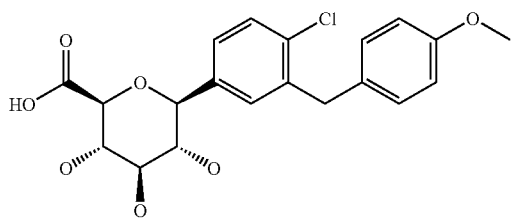

6-[4-chloro-3-(4-methoxy-benzyl)-phenyl]-3,45-trihydroxy-tetrahydro-pyran-2-carboxylic acid 2 mg 2,2,6,6-tetramethylpiperidin-1-yloxy followed by a solution of 76 mg potassium bromide and 0.10 g tetrabutylammonium bromide in 13.5 ml saturated sodium hydrogen carbonate solution are added to an ice-cold solution of 0.33 g 1-chloro-2-(4-methoxy-benzyl)-4-[2,3-O-(2,3-dimethoxy-but-2,3-diyl)-β-D-glucopyranos-1-yl]-benzene in 6.6 ml dichloromethane. A solution of 1.35 ml saturated aqueous sodium chloride solution, 0.65 ml saturated aqueous sodium hydrogen carbonate solution and 1.8 ml sodium hypochlorite solution (12% active chlorine) is added dropwise with vigorous stirring. After 1 and 2 h stirring a solution of 0.25 ml saturated aqueous sodium chloride solution, 0.13 ml saturated aqueous sodium hydrogen carbonate solution and 0.32 ml sodium hypochlorite solution (12% active chlorine) are added dropwise in each case. After another hour in the ice bath the solution is adjusted to pH=1 with 4 M hydrochloric acid and extracted with dichloromethane (1×) and ethyl acetate (3×). After drying on sodium sulphate the solvent is removed and the residue is taken up in 4 ml trifluoroacetic acid (80% in water). The solution is stirred for 2 h at ambient temperature and then diluted with water. The solution is evaporated to dryness, the residue is combined with 1 M hydrochloric acid and extracted with ethyl acetate. The organic phase is dried over sodium sulphate and the solvent is eliminated completely.

Yield: 0.16 g (60% of theory)

Mass spectrum (ESI$^+$): m/z=426/428 (chlorine) [M+NH$_4$]$^+$

EXAMPLE 14

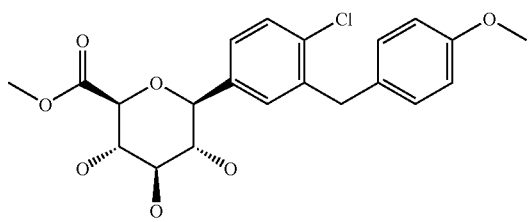

methyl 6-[4-chloro-3-(4-methoxy-benzyl)-phenyl]-3,4,5-trihydroxy-tetrahydro-pyran-2-carboxylate 90 mg potassium carbonate are added to a solution of 0.15 g 6-[4-chloro-3-(4-methoxy-benzyl)-phenyl]-3,4,5-trihydroxy-tetrahydro-pyran-2-carboxylic acid in 2 ml of dimethylformamide, and the mixture is stirred for 15 min at ambient temperature. Then 15 μl methyl iodide are added, and the mixture is stirred overnight. Then water is added and the mixture is extracted with ethyl acetate. After drying on sodium sulphate the solvent is removed and the residue is chromatographed (dichloromethane/methanol 1:0->10:1).

Yield: 0.07 g (47% of theory)

Mass spectrum (ESI$^+$): m/z=440/442 (chlorine) [M+NH$_4$]$^+$

EXAMPLE 15

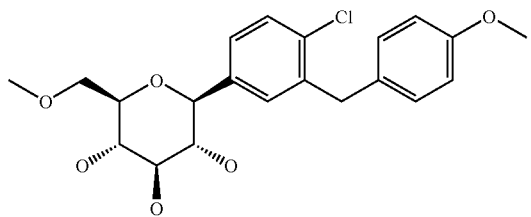

1-chloro-2-(4-methoxy-benzyl)-4-(6-O-methyl-β-D-glucopyranos-1-yl)-benzene

73 μl tetrafluoroboric acid (42% in water) are added to an ice-cold solution of 0.25 g 1-chloro-2-(4-methoxy-benzyl)-4-[3,4-O-(2,3-dimethoxy-but-2,3-diyl)-β-D-glucopyranos-1-yl]-benzene in 2 ml dichloromethane. Then 0.25 ml trimethylsilyldiazomethane in hexane (2 M) are slowly added dropwise. After 20 min stirring in the ice bath a further 0.13 ml, and after another 20 min another 0.06 ml and after another 20 min another 0.06 ml trimethylsilyldiazomethane (2 M in hexane) are added dropwise. After a further 30 min in the ice bath the mixture is diluted with water and the solution is extracted with dichloromethane. After drying on sodium sulphate the solvent is removed and the residue is taken up in 2.5 ml trifluoroacetic acid (80% in water). The solution is stirred for 2 h at ambient temperature and then neutralised with 4 M potassium hydroxide solution. The solution is extracted with ethyl acetate, the organic phase is dried over sodium sulphate and the solvent is eliminated. The residue is purified on silica gel (dichloromethane/methanol 1:0->20:1).

Yield: 0.10 g (50% of theory)

Mass spectrum (ESI$^+$): m/z=426/428 (chlorine) [M+NH$_4$]$^+$

The following compounds are also prepared analogously to the foregoing Examples and other methods known from the literature:

| No. | Structure |
| --- | --- |
| (9) | 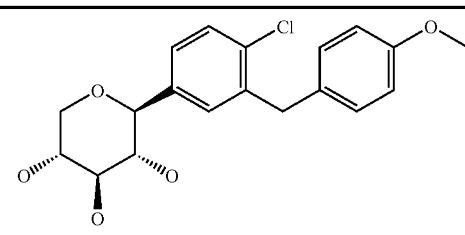 |
| (10) | 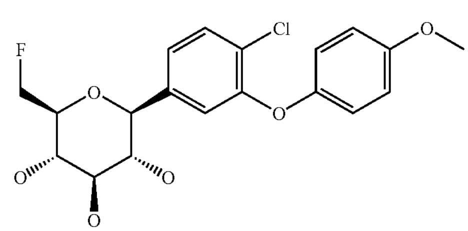 |

-continued

| No. | Structure |
|---|---|
| (11) | 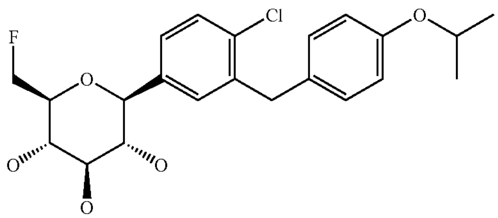 |
| (12) | 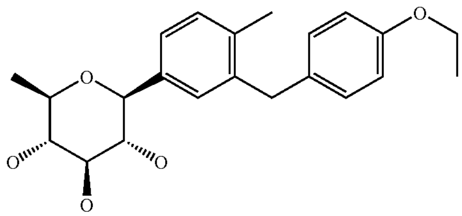 |
| (13) | 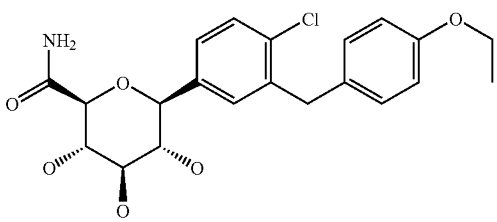 |
| (14) | 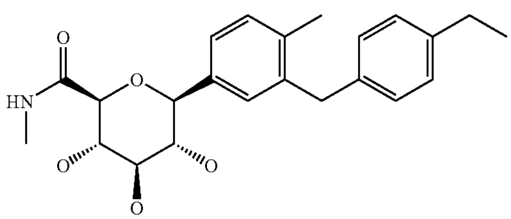 |
| (15) | 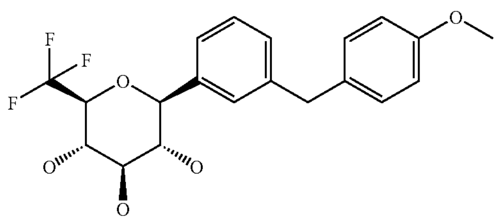 |
| (16) | 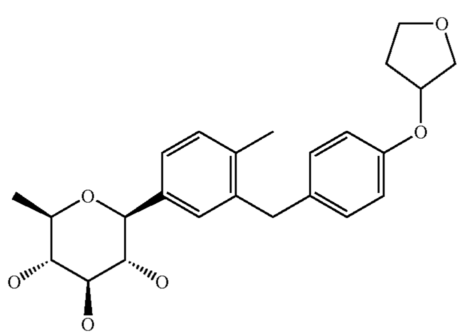 |

-continued

| No. | Structure |
|---|---|
| (17) | 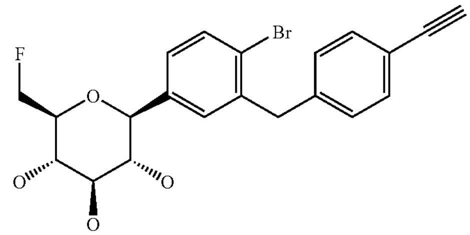 |
| (18) | 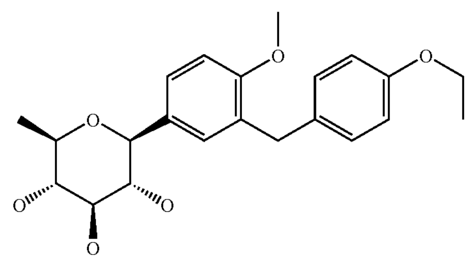 |
| (19) | 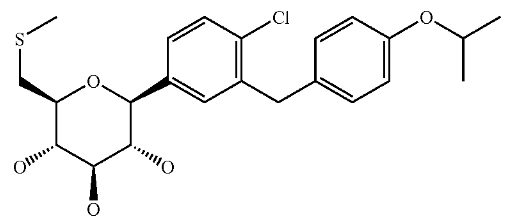 |
| (20) | 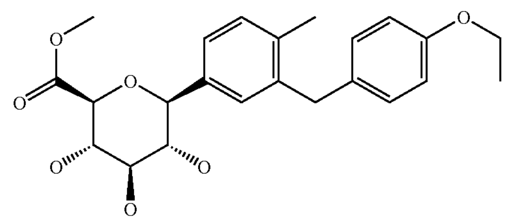 |
| (21) | 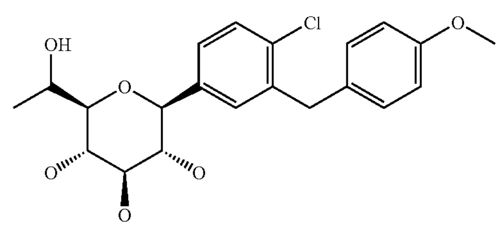 |
| (22) | 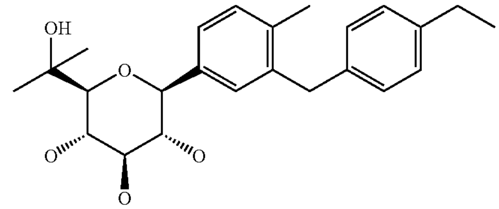 |

| No. | Structure |
|---|---|
| (23) | 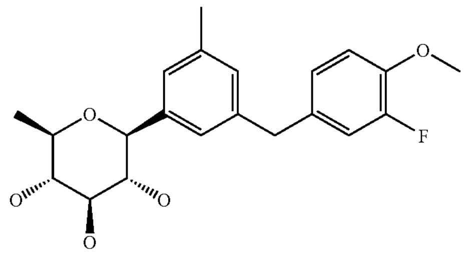 |
| (24) | 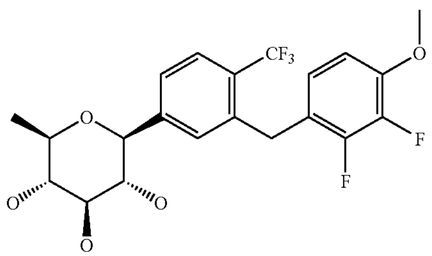 |
| (25) | 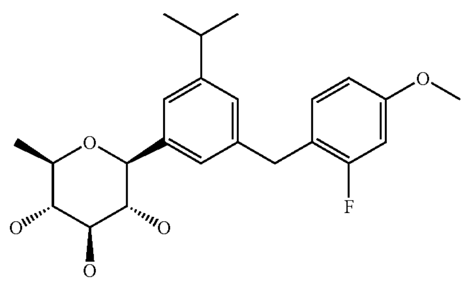 |
| (26) | 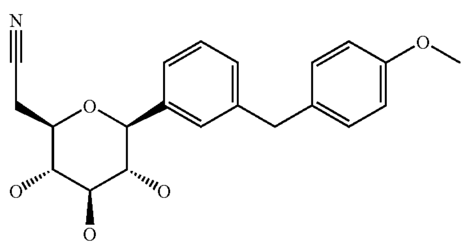 |
| (27) | 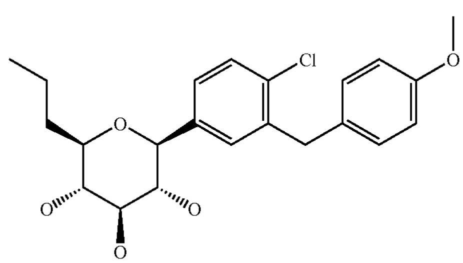 |
| (28) | 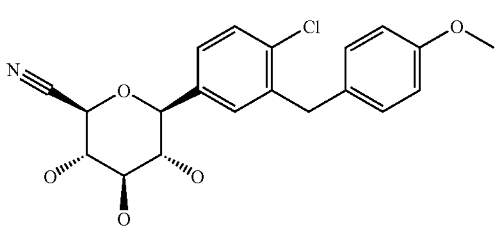 |
| (29) | |
| (30) | |
| (31) | |
| (32) | |
| (33) | |
| (34) | |

-continued

| No. | Structure |
|---|---|
| (35) | 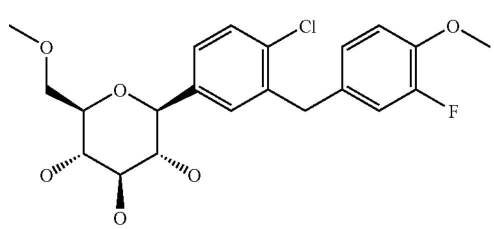 |
| (36) | 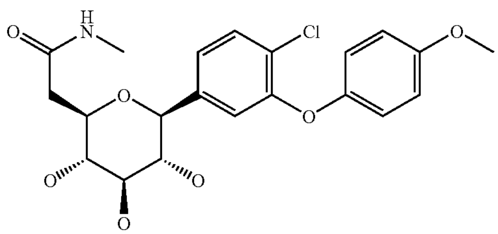 |
| (37) | 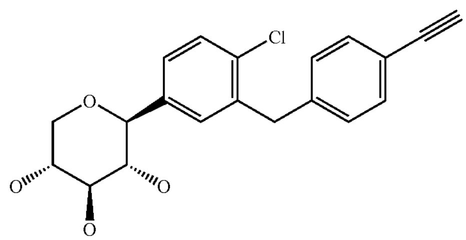 |
| (38) | 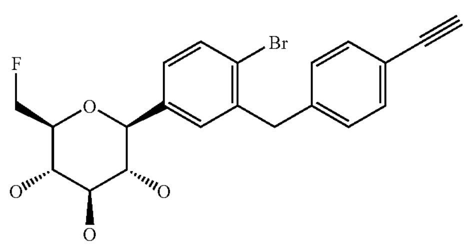 |
| (39) | 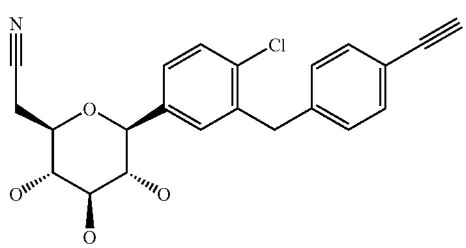 |
| (40) | 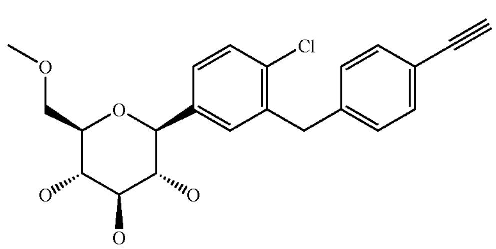 |

-continued

| No. | Structure |
|---|---|
| (41) | 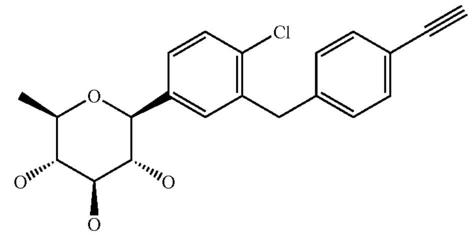 |
| (42) | 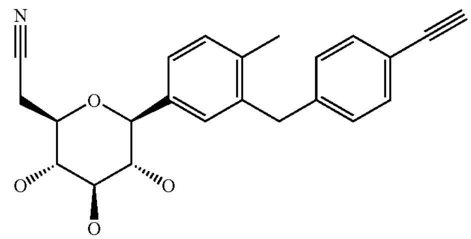 |
| (43) | 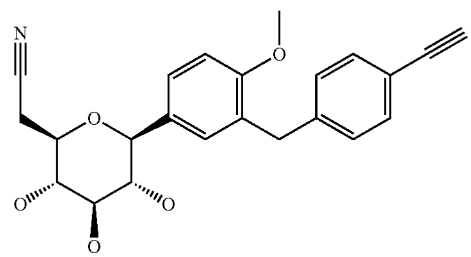 |
| (44) | 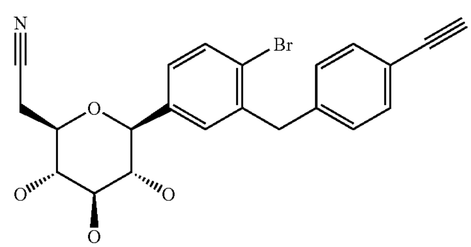 |
| (45) | 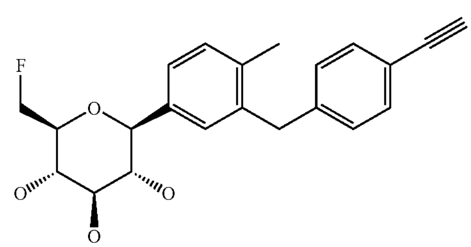 |
| (46) | 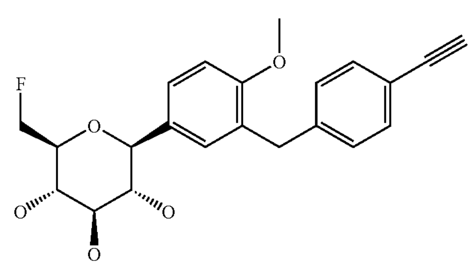 |

The following are examples of formulations in which the phrase "active substance" denotes one or more compounds according to the invention, including the salts thereof. In the case of one of the combinations with one or more other active substances the term "active substance" also includes the additional active substances.

EXAMPLE A

Tablets Containing 100 mg of Active Substance

Composition:
1 tablet contains:

| | |
|---|---:|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE B

Tablets Containing 150 mg of Active Substance

Composition:
1 tablet contains:

| | |
|---|---:|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

EXAMPLE C

Hard Gelatine Capsules Containing 150 mg of Active Substance 1 capsule contains:

| | |
|---|---:|
| active substance | 150.0 mg |
| corn starch (dried | approx. 180.0 mg |
| lactose (powdered) | approx 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

EXAMPLE D

Suppositories Containing 150 mg of Active Substance 1 suppository contains:

| | |
|---|---:|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE E

Ampoules Containing 10 mg Active Substance

Composition:

| | |
|---|---:|
| active substance | 10.0 mg |
| 0.01 N hydrochloric acid q.s. | |
| double-distilled water | ad 2.0 ml |

Preparation:

The active substance is dissolved in the necessary amount of 0.01 N HCl, made isotonic with common salt, filtered sterile and transferred into 2 ml ampoules.

EXAMPLE F

Ampoules Containing 50 mg of Active Substance

Composition:

| active substance | 50.0 mg |
|---|---|
| 0.01 N hydrochloric acid q.s. | |
| double-distilled water | ad 10.0 ml |

Preparation:

The active substance is dissolved in the necessary amount of 0.01 N HCl, made isotonic with common salt, filtered sterile and transferred into 10 ml ampoules.

The invention claimed is:

1. A D-Xylopyranosyl-substituted phenyl compound of formula I

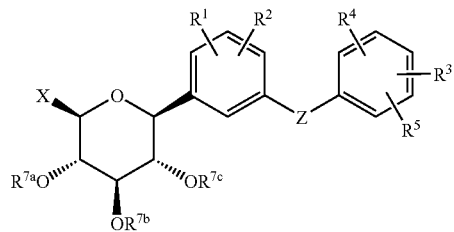

wherein $R^1$ denotes hydrogen, fluorine, chlorine, bromine, $C_{1-6}$-alkyl, $C_{2-6}$-alkynyl, $C_{2-6}$-alkenyl, $C_{3-7}$-cycloalkyl, $C_{3-7}$-cycloalkyl-$C_{1-3}$-alkyl, $C_{5-7}$-cycloalkenyl, $C_{5-7}$-cycloalkenyl-$C_{1-3}$-alkyl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, $C_{1-4}$-alkoxycarbonyl, amino, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, $C_{1-6}$-alkyloxy, $C_{3-7}$-cycloalkyloxy, $C_{5-7}$-cycloalkenyloxy, aryloxy, $C_{1-4}$-alkylsulphanyl, $C_{1-4}$-alkylsulphinyl, $C_{1-4}$-alkylsulphonyl, $C_{3-7}$-cycloalkylsulphanyl, $C_{3-7}$-cycloalkylsulphinyl, $C_{3-7}$-cycloalkylsulphonyl, $C_{5-7}$-cycloalkenylsulphanyl, $C_{5-7}$-cycloalkenylsulphinyl, $C_{5-7}$-cycloalkenylsulphonyl, arylsulphanyl, arylsulphinyl, arylsulphonyl, hydroxy, cyano or nitro, while alkyl, alkenyl, alkynyl, cycloalkyl and cycloalkenyl groups may be partly or completely fluorinated or may be mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, and $R^2$ denotes hydrogen, fluorine, chlorine, bromine, hydroxy, $C_{1-4}$-alkyl, $C_{1-4}$-alkoxy, cyano or nitro, while alkyl groups may be mono- or polysubstituted by fluorine, or in the event that $R^1$ and $R^2$ are bound to two C atoms of the phenyl ring which are adjacent to one another, $R^1$ and $R^2$ may be joined together in such a way that $R^1$ and $R^2$ together form a $C_{3-5}$-alkylene or $C_{3-5}$-alkenylene bridge, which may be partly or totally fluorinated or mono- or disubstituted by identical or different substituents selected from chlorine, hydroxy, $C_{1-3}$-alkoxy and $C_{1-3}$-alkyl and wherein one or two methylene groups may be replaced independently of one another by O, S, CO, SO, $SO_2$ or $NR^N$, $R^3$ denotes hydrogen, fluorine, chlorine, bromine, $C_{1-6}$-alkyl, $C_{2-6}$-alkynyl, $C_{2-6}$-alkenyl, $C_{3-7}$-cycloalkyl, $C_{3-7}$-cycloalkyl-$C_{1-3}$-alkyl, $C_{5-7}$-cycloalkenyl, $C_{5-7}$-cycloalkenyl-$C_{1-3}$-alkyl, aryl, heteroaryl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, hydroxycarbonyl, $C_{1-4}$-alkoxycarbonyl, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, arylcarbonylamino, heteroarylcarbonylamino, $C_{1-4}$-alkylsulphonylamino, arylsulphonylamino, $C_{1-6}$-alkoxy, $C_{3-7}$-cycloalkyloxy, $C_{5-7}$-cycloalkenyloxy, aryloxy, heteroaryloxy, $C_{1-4}$-alkylsulphanyl, $C_{1-4}$-alkylsulphinyl, $C_{1-4}$-alkylsulphonyl, $C_{3-7}$-cycloalkylsulphanyl, $C_{3-7}$-cycloalkylsulphinyl, $C_{3-7}$-cycloalkylsulphonyl, $C_{5-7}$-cycloalkenylsulphanyl, $C_{5-7}$-cycloalkenylsulphinyl, $C_{5-7}$-cycloalkenylsulphonyl, arylsulphanyl, arylsulphinyl, arylsulphonyl, amino, hydroxy, cyano or nitro, while alkyl, alkenyl, alkynyl, cycloalkyl and cycloalkenyl groups may be partly or totally fluorinated or mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, and $R^4$ denotes hydrogen, fluorine, chlorine, bromine, iodine, cyano, nitro, $C_{1-3}$-alkyl, $C_{1-3}$-alkoxy or methyl or methoxy substituted by 1 to 3 fluorine atoms, or in the event that $R^3$ and $R^4$ are bound to two C atoms of the phenyl ring which are adjacent to one another, $R^3$ and $R^4$ may be joined together in such a way that $R^3$ and $R^4$ together form a $C_{3-5}$-alkylene or $C_{3-5}$-alkenylene bridge, which may be partly or totally fluorinated or mono- or disubstituted by identical or different substituents selected from chlorine, hydroxy, $C_{1-3}$-alkoxy and $C_{1-3}$-alkyl and wherein one or two methylene groups may be replaced independently of one another by O, S, CO, SO, $SO_2$ or $NR^N$, $R^5$ denotes hydrogen, fluorine, chlorine, bromine, iodine, cyano, nitro, $C_{1-3}$-alkyl, $C_{1-3}$-alkoxy or methyl or methoxy substituted by 1 to 3 fluorine atoms, and $R^N$ independently of one another denote H or $C_{1-4}$-alkyl, L are selected independently of one another from among fluorine, chlorine, bromine, iodine, $C_{1-3}$-alkyl, difluoromethyl, trifluoromethyl, $C_{1-3}$-alkoxy, difluoromethoxy, trifluoromethoxy and cyano, $R^{7a}$, $R^{7b}$, and $R^{7c}$ independently of one another have a meaning selected from among hydrogen, ($C_{1-18}$-alkyl)carbonyl, ($C_{1-18}$-alkyl)oxycarbonyl, arylcarbonyl and aryl-($C_{1-3}$-alkyl)-carbonyl, X denotes hydrogen, $C_{1-6}$-alkyl, $C_{2-6}$-alkynyl, $C_{2-6}$-alkenyl, $C_{3-7}$-cycloalkyl, $C_{3-7}$-cycloalkyl-$C_{1-3}$-alkyl, $C_{5-7}$-cycloalkenyl, $C_{5-7}$-cycloalkenyl-$C_{1-3}$-alkyl, aryl, aryl-$C_{1-3}$-alkyl, heteroaryl, heteroaryl-$C_{1-3}$-alkyl, $C_{1-4}$-alkylcarbonyl, arylcarbonyl, aminocarbonyl, $C_{1-4}$-alkylaminocarbonyl, di-($C_{1-3}$-alkyl)aminocarbonyl, (aryl-$C_{1-3}$-alkyl)aminocarbonyl, pyrrolidin-1-ylcarbonyl, piperidin-1-ylcarbonyl, morpholin-4-ylcarbonyl, hydroxycarbonyl, $C_{1-4}$-alkoxycarbonyl, $C_{1-4}$-alkylcarbonylamino-$C_{1-3}$-alkyl, N-($C_{1-4}$-alkylcarbonyl)-N-($C_{1-3}$-alkyl)-amino-$C_{1-3}$-alkyl, arylcarbonylamino-$C_{1-3}$-alkyl, $C_{1-4}$-alkylsulphonylamino-$C_{1-3}$-alkyl, arylsulphonylamino-$C_{1-3}$-alkyl, $C_{1-6}$-alkoxy-$C_{1-3}$-alkyl, $C_{3-7}$-cycloalkyloxy-$C_{1-3}$-alkyl, $C_{5-7}$-cycloalkenyloxy-$C_{1-3}$-alkyl, aryloxy-$C_{1-3}$-alkyl, heteroaryloxy-$C_{1-3}$-alkyl, $C_{1-4}$-alkylsulphanyl-$C_{1-3}$-alkyl, $C_{1-4}$-alkylsulphinyl-$C_{1-3}$-alkyl, $C_{1-4}$-alkylsulphinyl, $C_{1-4}$-alkylsulphonyl, $C_{1-4}$-alkylsulphonyl-$C_{1-3}$-alkyl, $C_{1-4}$-arylsulphanyl-$C_{1-3}$-alkyl, arylsulphonyl-$C_{1-3}$-alkyl, aryl-$C_{1-3}$-alkylsulphonyl-$C_{1-3}$-alkyl, $C_{1-4}$-alkylsulphonyloxy-$C_{1-3}$-alkyl, arylsulphonyloxy-$C_{1-3}$-alkyl, aryl-$C_{1-3}$-alkylsulphonyloxy-$C_{1-3}$-alkyl, $C_{3-7}$-cycloalkylsulphanyl-$C_{1-3}$-alkyl, $C_{3-7}$-cycloalkylsulphinyl, $C_{3-7}$-cycloalkylsulphonyl, $C_{5-7}$-cycloalkenylsulphanyl-$C_{1-3}$-alkyl, $C_{5-7}$-cycloalkenylsulphinyl, $C_{5-7}$-cycloalkenylsulphonyl, $C_{1-4}$-alkylcarbonylsulphanyl-$C_{1-3}$-alkyl or cyano, while alkyl, alkenyl, alkynyl, cycloalkyl and cycloalkenyl groups may be partly or totally fluorinated or mono- or disubstituted by identical or different substituents selected from chlorine, cyano, hydroxy, mercapto, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, and provided that X representing hydroxymethyl is excluded, Z denotes oxygen, methylene, dimethylmethylene, difluoromethylene or carbonyl;

while the term aryl groups used in the definition of the above groups denotes phenyl or naphthyl groups, which may be mono- or disubstituted independently of one another by identical or different groups L; and the term heteroaryl groups used in the definition of the above-mentioned groups denotes a pyrrolyl, furanyl, thienyl, pyridyl, indolyl, benzofuranyl, benzothiophenyl, quinolinyl or isoquinolinyl group, or a pyrrolyl, furanyl, thienyl, pyridyl or imidazolyl group, wherein one or two methyne groups are replaced by nitrogen atoms, or an indolyl, benzofuranyl, benzothiophenyl, quinolinyl or isoquinolinyl group, wherein one to three methyne groups are replaced by nitrogen atoms, while the above-mentioned heteroaryl groups may be mono- or disubstituted independently of one another by identical or different groups L;

while by the N-heterocycloalkyl group mentioned in the definition of the above-mentioned groups is meant a saturated carbocyclic ring which comprises an imino group in the ring, which may comprise another optionally substituted imino group or an O or S atom in the ring, and unless otherwise stated the above-mentioned alkyl groups may be straight-chain or branched, or a tautomer or stereoisomer thereof or mixtures thereof or a salt thereof.

2. A D-Xylopyranosyl-substituted phenyl compound according to claim 1, of formula I.2

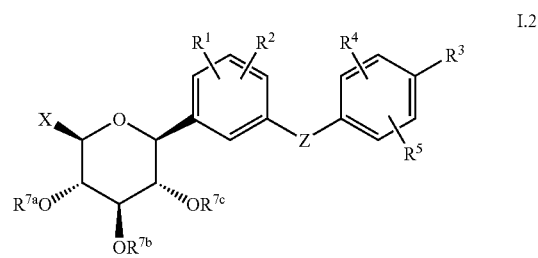

wherein $R^1$ to $R^5$, X, Z, $R^{7a}$, $R^{7b}$, $R^{7c}$ have the meanings according to claim 1.

3. A D-Xylopyranosyl-substituted phenyl compound according to claim 1, of formula I.2c

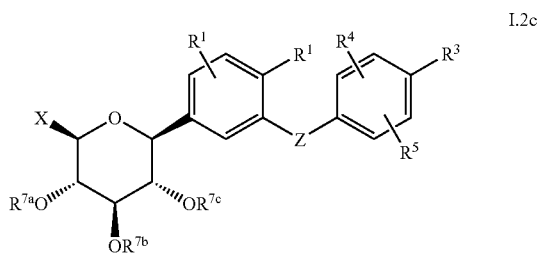

wherein $R^1$ to $R^5$, X, Z, $R^{7a}$, $R^{7b}$, $R^{7c}$ have the meanings according to claim 1.

4. A D-Xylopyranosyl-substituted phenyl compound according to claim 1, wherein $R^1$ denotes hydrogen, fluorine, chlorine, bromine, $C_{1-6}$-alkyl, $C_{2-6}$-alkynyl, $C_{2-6}$-alkenyl, $C_{3-7}$-cycloalkyl, $C_{5-7}$-cycloalkenyl, $C_{1-6}$-alkyloxy, $C_{3-7}$-cycloalkyloxy or cyano, while in cycloalkyl and cycloalkenyl groups one or two methylene units optionally replaced independently of one another by O or CO and alkyl, alkenyl and alkynyl groups may be partly or totally fluorinated.

5. A D-Xylopyranosyl-substituted phenyl compound according to claim 1 wherein $R^3$ denotes $C_{1-6}$-alkyl, $C_{2-6}$-alkynyl, $C_{1-4}$-alkyloxy, $C_{3-7}$-cycloalkyl, $C_{3-7}$-cycloalkyloxy or hydroxy, while in said cycloalkyl groups one or two methylene units may be replaced independently of one another by O or CO and said alkyl groups may be partly or totally fluorinated.

6. A D-Xylopyranosyl-substituted phenyl compound according to claim 1, wherein X denotes hydrogen, cyano, $C_{1-6}$-alkyl, $C_{2-6}$-alkynyl, $C_{2-6}$-alkenyl, $C_{1-4}$-alkylcarbonyl, $C_{1-4}$-alkoxycarbonyl, aminocarbonyl, $C_{1-4}$-alkylaminocarbonyl, di-($C_{1-4}$-alkyl)aminocarbonyl or $C_{1-4}$-alkylcarbonylamino-$C_{1-3}$-alkyl, while alkyl groups may be mono- or polyfluorinated or monosubstituted by chlorine or cyano and when X denotes alkyl with 2 or more C atoms, it may be substituted by a hydroxy substituent.

7. A D-Xylopyranosyl-substituted phenyl compound according to claim 1, wherein
X denotes $C_{1-4}$-alkyloxymethyl, $C_{3-7}$-cycloalkyloxymethyl or aryloxymethyl,
while by the aryl group is meant a phenyl or naphthyl group, which may be mono- or disubstituted by identical or different groups L and L is defined according to claim 1.

8. A D-Xylopyranosyl-substituted phenyl compound according to claim 1, wherein
X denotes mercaptomethyl, $C_{1-4}$-alkylsulphanylmethyl or $C_{1-4}$-alkylcarbonylsulphanylmethyl.

9. A D-Xylopyranosyl-substituted phenyl compound according to claim 1, wherein
X denotes chloromethyl, bromomethyl, iodomethyl, $C_{1-6}$-alkylsulphonyloxymethyl, arylsulphonyloxymethyl or aryl-$C_{1-3}$-alkyl-sulphonyloxymethyl,
while the above-mentioned alkyl groups may be partly or totally fluorinated or mono- or dichlorinated and the above-mentioned aryl groups may be mono- or disubstituted by identical or different groups L, while L selected from the group consisting of among fluorine, chlorine, bromine, iodine, $C_{1-3}$-alkyl, difluoromethyl, trifluoromethyl and cyano.

10. A D-Xylopyranosyl-substituted phenyl compound according to claim 1, wherein
$R^2$ denotes hydrogen, fluorine, hydroxy, methoxy, ethoxy or methyl.

11. A D-Xylopyranosyl-substituted phenyl compound according to claim 1, wherein
$R^4$ and $R^5$ independently of one another represent hydrogen or fluorine.

12. A D-Xylopyranosyl-substituted phenyl compound according to claim 1, wherein
Z denotes oxygen or methylene.

13. A D-Xylopyranosyl-substituted phenyl compound according to claim 1, wherein
$R^{7a}$, $R^{7b}$, $R^{7c}$ independently of one another represent hydrogen, ($C_{1-6}$-alkyl)oxycarbonyl, ($C_{1-8}$-alkyl)carbonyl or benzoyl.

14. A physiologically acceptable salt of a compound according to claim 1 with an inorganic or organic acid.

15. A pharmaceutical composition comprised of a compound according to claim 1 or a physiologically acceptable salt thereof and one or more inert carriers and/or diluents.

16. A pharmaceutical composition according to claim 15 wherein the inert carrier or diluent is incorporated by a nonchemical method.

17. A method of treating a metabolic disorder selected from the group consisting of type 1 or type 2 diabetes mellitus, complications of diabetes, and reactive hypoglycaemia, said method comprised of the step of administering to a patient in need thereof a therapeutic amount of a pharmaceutical composition comprised of a compound according to claim 1 or a physiologically acceptable salt thereof.

18. A method according to claim 17 wherein the metabolic disorder is type 1 or type 2 diabetes mellitus.

19. A Method of inhibiting the sodium-dependent glucose cotransporter SGLT in a cell by administration of an effective amount of a compound according to claim 1 or a physiologically acceptable salt thereof.

20. A method of reducing the incidence of degeneration of pancreatic beta cells and/or for improving the functionality of pancreatic beta cells, said method comprised of the steps of administering to a patient in need thereof a therapeutic amount of a compound according to claim 1 or a physiologically acceptable salt thereof.

21. A process for preparing a compound formula I according to claim 1 or a tautomer or stereoisomer thereof or mixtures thereof or a salt therof, comprised of the steps of reacting a compound according to formula II:

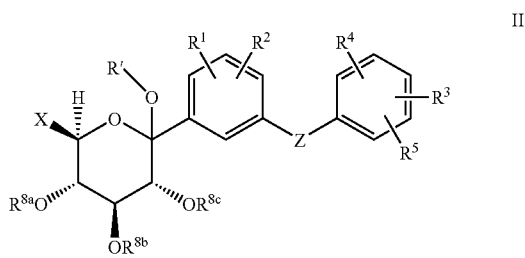

wherein
R' denotes H, $C_{1-4}$-alkyl, ($C_{1-18}$-alkyl)carbonyl, ($C_{1-18}$-alkyl)oxycarbonyl, arylcarbonyl or aryl-($C_{1-3}$-alkyl)carbonyl, wherein the alkyl or aryl groups may be mono- or polysubstituted by halogen;

$R^{8a}$, $R^{8b}$, and $R^{8c}$ independently of one another have one of the meanings given for the groups $R^{7a}$, $R^{7b}$, $R^{7c}$, denote a benzyl group or an $R^a R^b R^c Si$ group or a ketal or acetal group, while in each case two adjacent groups $R^{8a}$, $R^{8b}$, $R^{8c}$, and $R^{8d}$ may form a cyclic ketal or acetal group or a 1,2-di($C_{1-3}$-alkoxy)-1,2-di($C_{1-3}$-alkyl)-ethylene bridge, while the above-mentioned ethylene bridge together with two oxygen atoms and the associated two carbon atoms of the pyranose ring form a substituted dioxane ring, and while alkyl, aryl and/or benzyl groups may be mono- or polysubstituted by halogen or $C_{1-3}$-alkoxy and benzyl groups may also be substituted by a di-($C_{1-3}$-alkyl) amino group; and $R^a$, $R^b$, $R^c$ independently of one another represent $C_{1-4}$-alkyl, aryl or aryl-$C_{1-3}$-alkyl, wherein the aryl or alkyl groups may be mono- or polysubstituted by halogen;

while the term aryl groups used in the definition of the above groups denotes phenyl or naphthyl groups, and X, Z, $R^1$ to $R^5$, $R^{7a}$, $R^{7b}$, and $R^{7c}$ have the meanings given in claim 1, with a reducing agent in the presence of an acid, and any protective groups present are cleaved at the same time or subsequently;

optionally, cleaving any protective group and/or optionally, selectively derivatizing a compound of formula I at a hydroxy group or substituting a hydroxy group and/or optionally, resolving a compound of formula I thus obtained into its stereoisomers and/or optionally, converting a compound of formula I thus obtained into a physiologically acceptable salt thereof.

22. A process for preparing a compound of formula I according to claim 1 or a tautomer or stereoisomer therof or mixtures thereof or salt thereof, wherein $R^{7a}$, $R^{7b}$ and $R^{7c}$ represent hydrogen, said method comprised of the steps of removing the groups $R^{8a}$, $R^{8b}$ or $R^{8c}$ which do not represent hydrogen from a compound of formula III

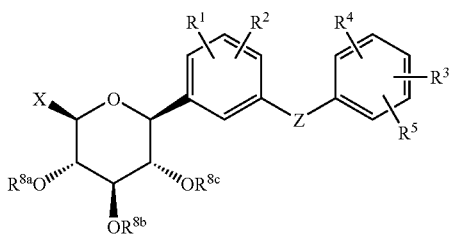

III wherein $R^{8a}$, $R^{8b}$, and $R^{8c}$ independently of one another have one of the meanings given for the groups $R^{7a}$, $R^{7b}$, and $R^{7c}$, denote a benzyl group or an $R^a R^b R^c Si$ group or a ketal or acetal group, while in each case two adjacent groups $R^{8a}$, $R^{8b}$, $R^{8c}$, and $R^{8d}$ may form a cyclic ketal or acetal group or a 1,2-di($C_{1-3}$-alkoxy)-1,2-di($C_{1-3}$-alkyl)-ethylene bridge, while the above-mentioned ethylene bridge together with two oxygen atoms and the associated two carbon atoms of the pyranose ring form a substituted dioxane ring, and while alkyl, aryl and/or benzyl groups may be mono- or polysubstituted by halogen or $C_{1-3}$-alkoxy and benzyl groups may also be substituted by a di-($C_{1-3}$-alkyl)amino group; and wherein at least one of the groups $R^{8a}$, $R^{8b}$, and $R^{8c}$ does not represent hydrogen; and $R^a$, $R^b$, and $R^c$ independently of one another represent $C_{1-4}$-alkyl, aryl or aryl-$C_{1-3}$-alkyl, wherein the aryl or alkyl groups may be mono- or polysubstituted by halogen;

while the term aryl groups used in the definition of the above groups denotes phenyl or naphthyl groups, and X, Z, $R^1$ to $R^5$, $R^{7a}$, $R^{7b}$, and $R^{7c}$ have the meanings given in claim 1, and optionally cleaving said compound of any protective group of formula III, and/or, optionally selectively derivatizing at a hydroxy group or substituting a hydroxy group and/or, optionally resolving said compound obtained into its stereoisomers, and/or, optionally converting said compound into its a physiologically acceptable salt thereof.

23. A process according to claim 21, wherein at least one of $R^{8a}$, $R^{8b}$, and $R^{8c}$ is an alkylidene or arylalkylidene ketal or acetal group or two adjacent groups $R^{8a}$, $R^{8b}$, $R^{8c}$, and $R^{8d}$ form a 2,3-dimethyl-2,3-di($C_{1-3}$-alkoxy)-1,4-dioxane ring.

24. A process according to claim 22, wherein at least one of $R^{8a}$, $R^{8b}$, and $R^{8c}$ is an alkylidene or arylalkylidene ketal or acetal group or two adjacent groups $R^{8a}$, $R^{8b}$, $R^{8c}$, and $R^{8d}$ form a 2,3-dimethyl-2,3-di($C_{1-3}$-alkoxy)-1,4-dioxane ring.

* * * * *